US010052106B2

(12) United States Patent
Binmoeller et al.

(10) Patent No.: US 10,052,106 B2
(45) Date of Patent: Aug. 21, 2018

(54) DEVICES AND METHODS FOR FORMING AN ANASTOMOSIS

(71) Applicant: XLUMENA, INC., Mountain View, CA (US)

(72) Inventors: Kenneth F. Binmoeller, San Francisco, CA (US); Peter Brown, Palo Alto, CA (US); Keke Lepulu, Menlo Park, CA (US); Ryan Donovan, Santa Clara, CA (US)

(73) Assignee: XLUMENA, INC., Mountain View, CA (US)

( * ) Notice: Subject to any disclaimer, the term of this patent is extended or adjusted under 35 U.S.C. 154(b) by 0 days.

(21) Appl. No.: 15/331,285

(22) Filed: Oct. 21, 2016

(65) Prior Publication Data

US 2017/0035428 A1 Feb. 9, 2017

Related U.S. Application Data

(63) Continuation of application No. 14/186,994, filed on Feb. 21, 2014.

(Continued)

(51) Int. Cl.
*A61M 5/00* (2006.01)
*A61B 17/11* (2006.01)
(Continued)

(52) U.S. Cl.
CPC ........ *A61B 17/1114* (2013.01); *A61F 5/0076* (2013.01); *A61B 2017/00004* (2013.01);
(Continued)

(58) Field of Classification Search
CPC .............. A61B 17/083; A61B 17/1114; A61B 2090/306; A61B 2090/378;
(Continued)

(56) References Cited

U.S. PATENT DOCUMENTS 5,246,445 A 9/1993 Yachia et al.
5,681,345 A 10/1997 Euteneuer
(Continued)

FOREIGN PATENT DOCUMENTS

CN 1575155 A 2/2005
CN 2845770 Y 12/2006
(Continued)

OTHER PUBLICATIONS

Supplementary Partial European Search Report dated (Nov. 18, 2016), for application number (7 pages).
(Continued)

*Primary Examiner* — Philip R Wiest

(57) ABSTRACT

Devices and methods for deploying an anastomotic stent between portions of the gastrointestinal (GI) tract are disclosed. The anastomotic stents are configured to atraumatically engage the tissue walls and to permit the flow of fluid, partially digested food, and food. The stents can be deployed using endoscopic catheter devices, laparoscopic tools, and combinations of both endoscopic tools and laparoscopic tools. Examples of anastomoses include anastomoses between the stomach and a portion of the intestines such as the jejunum. Anastomoses can also be formed between two closed ends of the intestines, such as two closed ends of the colon formed during a colon resection procedure. Anastomoses can also be formed between a fundal pouch formed during a gastric bypass procedure and the jejunum. Laparoscopic tools are disclosed to deploy a stent by selectively removing a radial restraint on a self expanding stent with the restraint removed through the laparoscopic access points.

15 Claims, 37 Drawing Sheets

Related U.S. Application Data

(60) Provisional application No. 61/767,577, filed on Feb. 21, 2013.

(51) Int. Cl.
*A61F 5/00* (2006.01)
*A61B 17/00* (2006.01)
*A61B 90/30* (2016.01)
*A61B 90/00* (2016.01)

(52) U.S. Cl.
CPC ............... *A61B 2017/0034* (2013.01); *A61B 2017/00278* (2013.01); *A61B 2017/00477* (2013.01); *A61B 2017/00867* (2013.01); *A61B 2017/00876* (2013.01); *A61B 2017/1132* (2013.01); *A61B 2017/1135* (2013.01); *A61B 2017/1139* (2013.01); *A61B 2090/306* (2016.02); *A61B 2090/378* (2016.02); *A61B 2090/3925* (2016.02)

(58) Field of Classification Search
CPC ........... A61B 2017/00004; A61B 2017/00278; A61B 2017/0034; A61B 2017/00477; A61B 2017/00867; A61B 2017/00876; A61B 2017/1132; A61B 2017/1135; A61B 2017/1139; A61F 5/0076
USPC ......................................................... 604/8, 9
See application file for complete search history.

(56) References Cited

U.S. PATENT DOCUMENTS

| | | | |
|---|---|---|---|
| 5,709,713 | A | 1/1998 | Evans et al. |
| 6,063,113 | A | 5/2000 | Kavteladze et al. |
| 6,152,144 | A | 11/2000 | Lesh et al. |
| 6,315,708 | B1 | 11/2001 | Salmon et al. |
| 6,468,303 | B1 | 10/2002 | Amplatz et al. |
| 6,517,558 | B2 | 2/2003 | Gittings et al. |
| 6,846,323 | B2 | 1/2005 | Yip et al. |
| 2003/0199991 | A1 | 10/2003 | Stack et al. |
| 2003/0216749 | A1 | 11/2003 | Ishikawa et al. |
| 2005/0022843 | A1 | 2/2005 | Policicchio et al. |
| 2006/0253088 | A1 | 11/2006 | Chow et al. |
| 2007/0096048 | A1 | 5/2007 | Clerc et al. |
| 2007/0112380 | A1 | 5/2007 | Figulla et al. |
| 2008/0132999 | A1 | 6/2008 | Mericle et al. |
| 2008/0140172 | A1 | 6/2008 | Carpenter |
| 2008/0215089 | A1 | 9/2008 | Williams et al. |
| 2008/0249562 | A1 | 10/2008 | Cahill |
| 2009/0062841 | A1 | 3/2009 | Amplatz et al. |
| 2009/0082803 | A1 | 3/2009 | Adams et al. |
| 2009/0138071 | A1 | 5/2009 | Cheng et al. |
| 2009/0216265 | A1 | 8/2009 | DeVries et al. |
| 2010/0023046 | A1 | 1/2010 | Heidner et al. |
| 2010/0191167 | A1 | 7/2010 | Laufer |
| 2010/0241218 | A1 | 9/2010 | Bruszewski et al. |
| 2010/0268316 | A1* | 10/2010 | Brenneman .......... A61B 17/083 623/1.11 |
| 2011/0060398 | A1 | 3/2011 | Tupil et al. |
| 2011/0282461 | A1 | 11/2011 | Shin et al. |
| 2013/0012969 | A1* | 1/2013 | Shin ...................... A61B 17/11 606/155 |

FOREIGN PATENT DOCUMENTS

| | | |
|---|---|---|
| CN | 2925418 Y | 7/2007 |
| CN | 101951856 A | 1/2011 |
| EP | 2543323 A1 | 9/2013 |
| JP | 2000237303 | 9/2000 |
| JP | 2002542872 A | 12/2002 |
| WO | 2001021247 | 3/2001 |
| WO | 2010138277 A2 | 3/2003 |
| WO | 2005006990 A2 | 1/2005 |
| WO | 2006081448 A1 | 8/2006 |
| WO | 2008/005510 | 1/2008 |
| WO | 2009091425 A1 | 7/2009 |
| WO | 2009140195 A1 | 11/2009 |
| WO | 2010115011 A1 | 7/2010 |
| WO | 2010115011 A1 | 10/2010 |
| WO | 2011044486 A1 | 4/2011 |
| WO | 2014176458 A2 | 10/2014 |

OTHER PUBLICATIONS

Article 153(7) EPC dated (Feb. 23, 2017) for 14754916.6 (11 pages).

Rieder E. et al., 'Endoscopic suture fixation of gastrointestinal stents: proof of biomechanical principles and early clinical experience', Endoscopy, 2012, vol. 44, 6 pages.

* cited by examiner

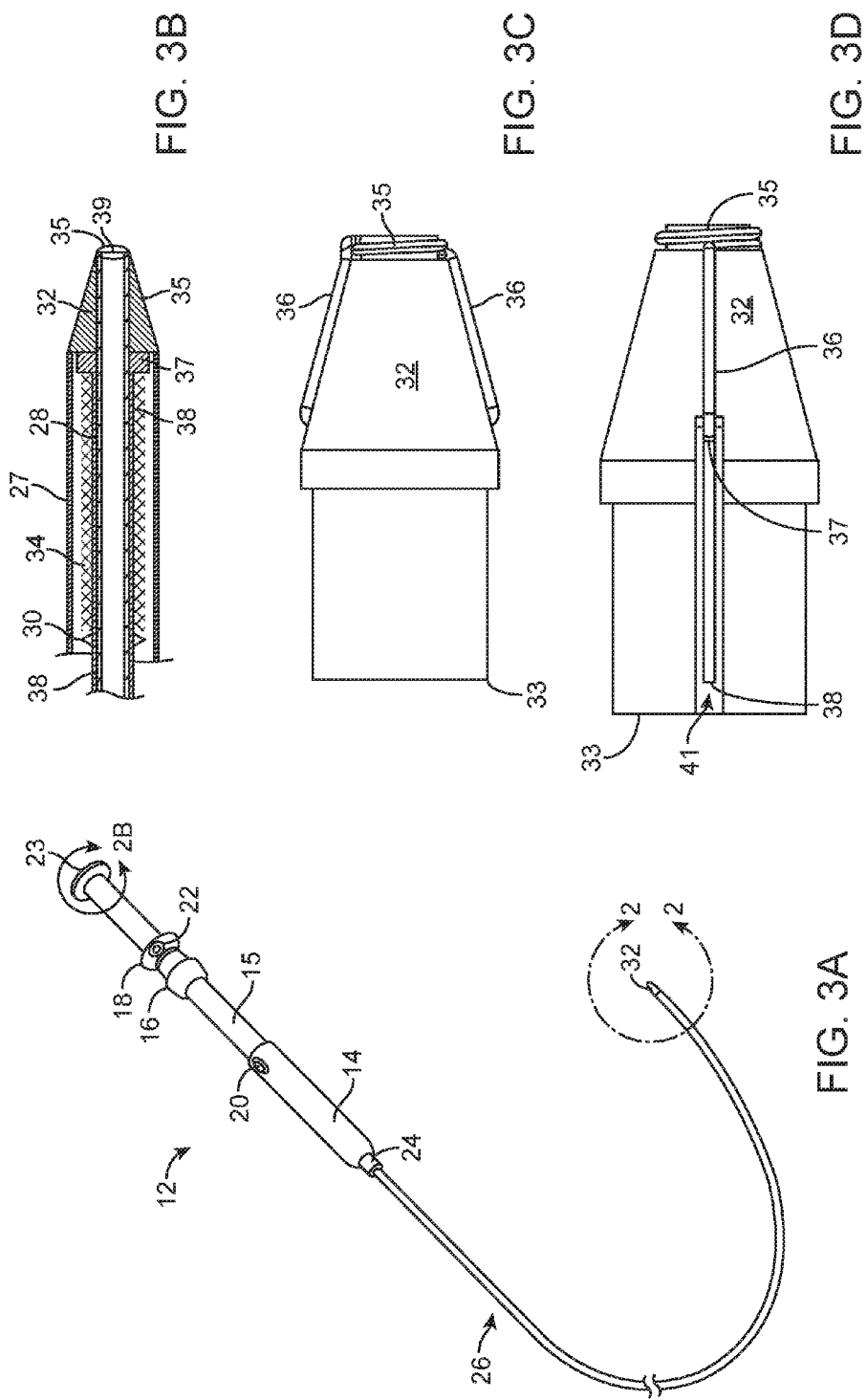

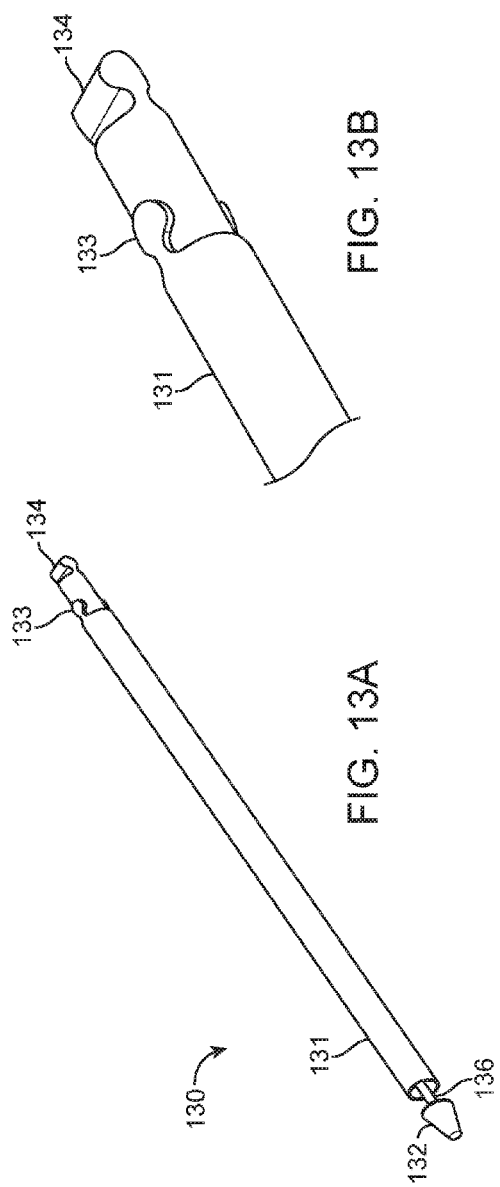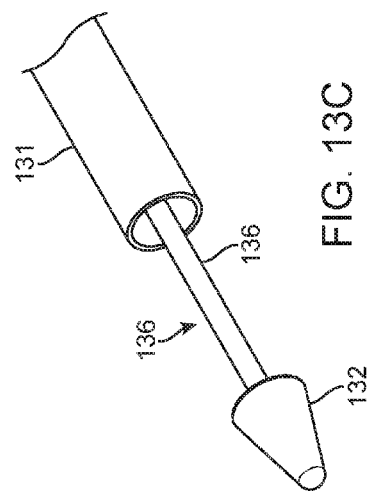

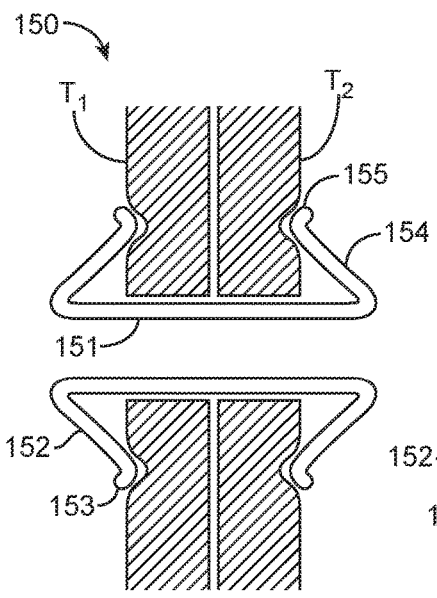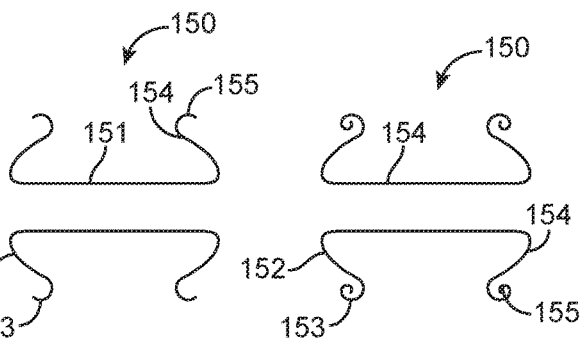
FIG. 15A  FIG. 15B  FIG. 15C
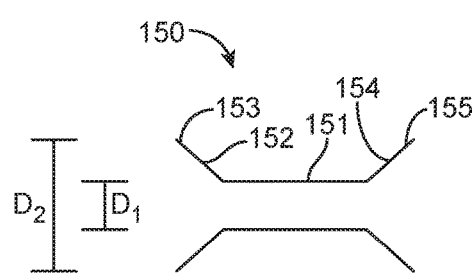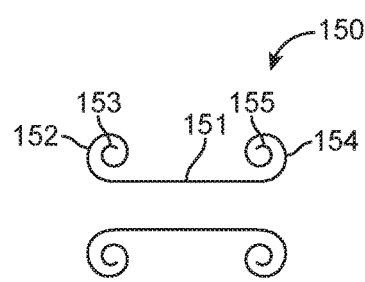
FIG. 15D  FIG. 15E
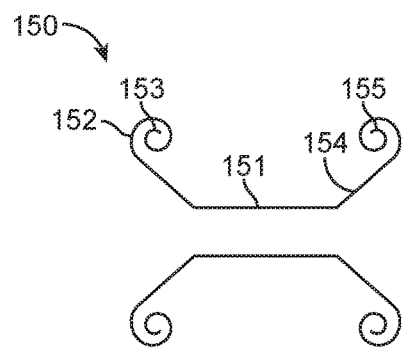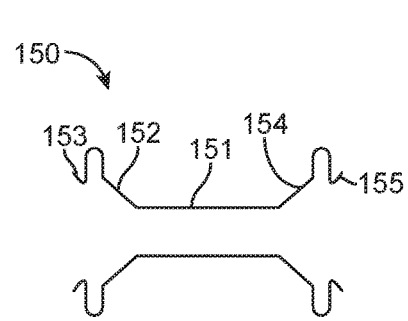
FIG. 15F  FIG. 15G

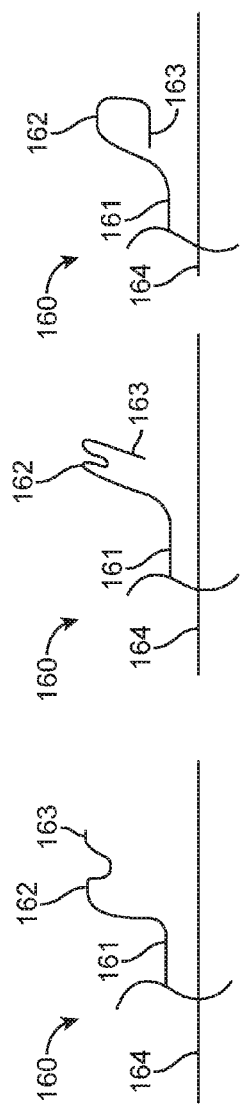
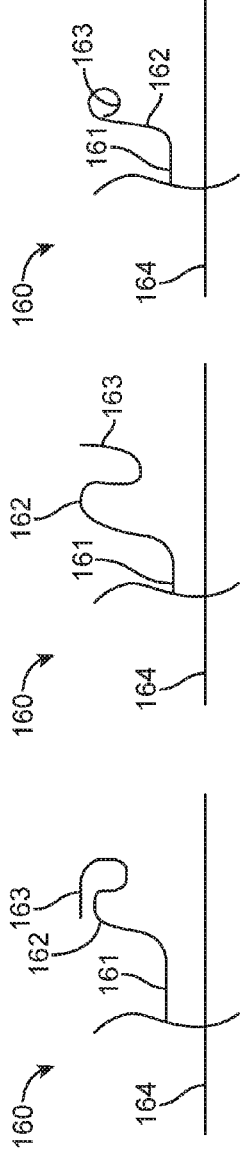
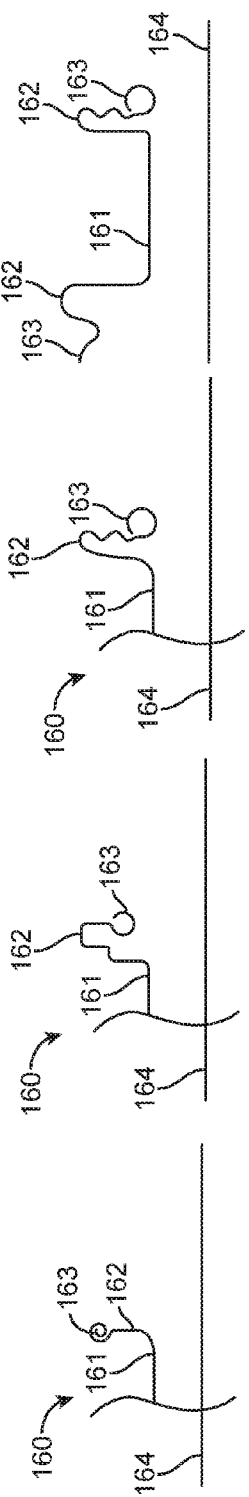
FIG. 16A FIG. 16B FIG. 16C
FIG. 16D FIG. 16E FIG. 16F
FIG. 16G FIG. 16H FIG. 16I
FIG. 16J

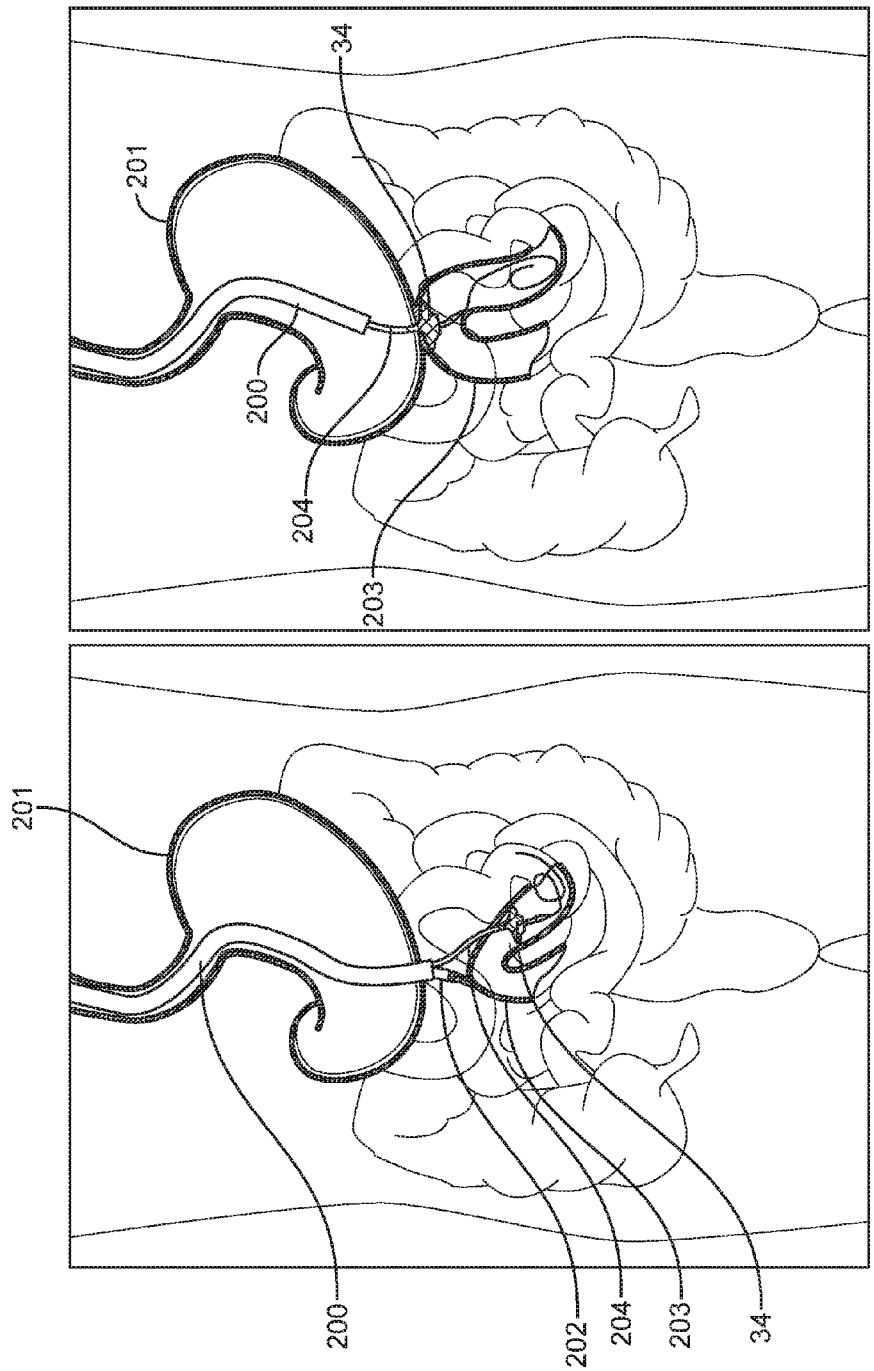

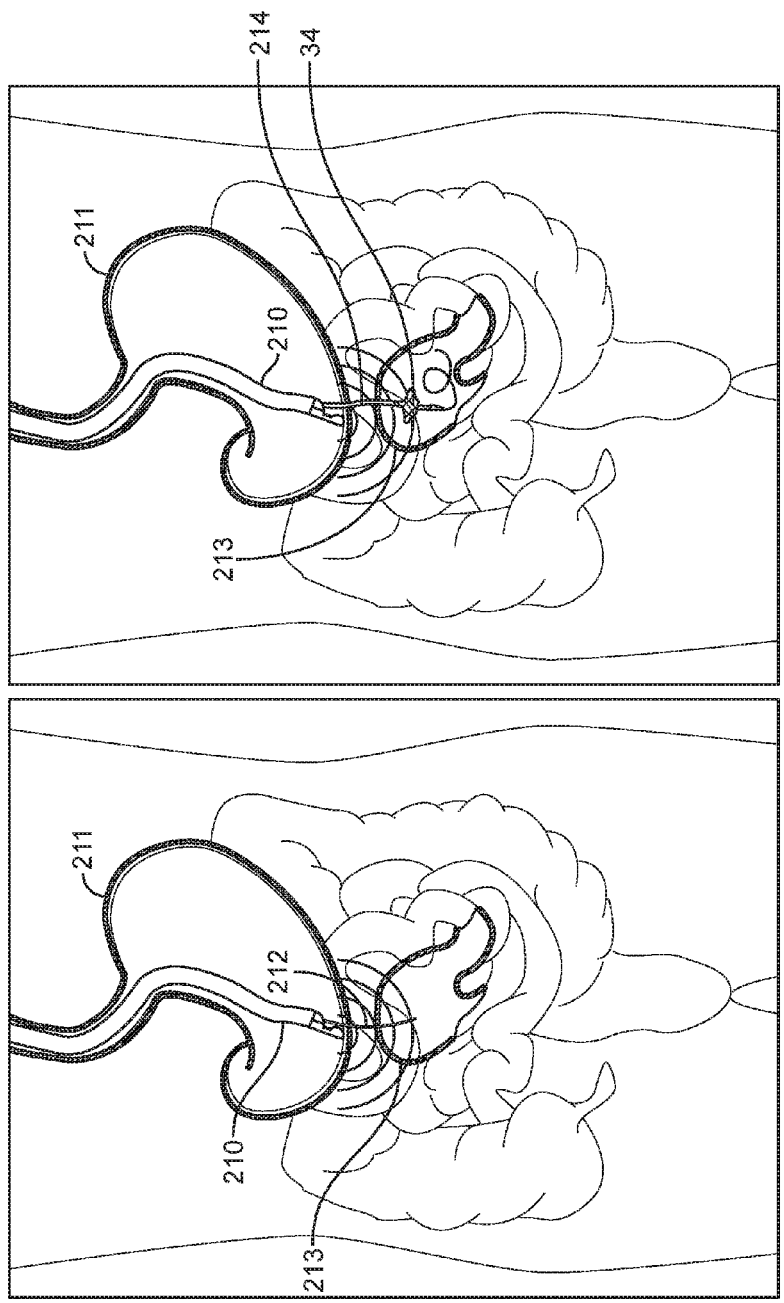

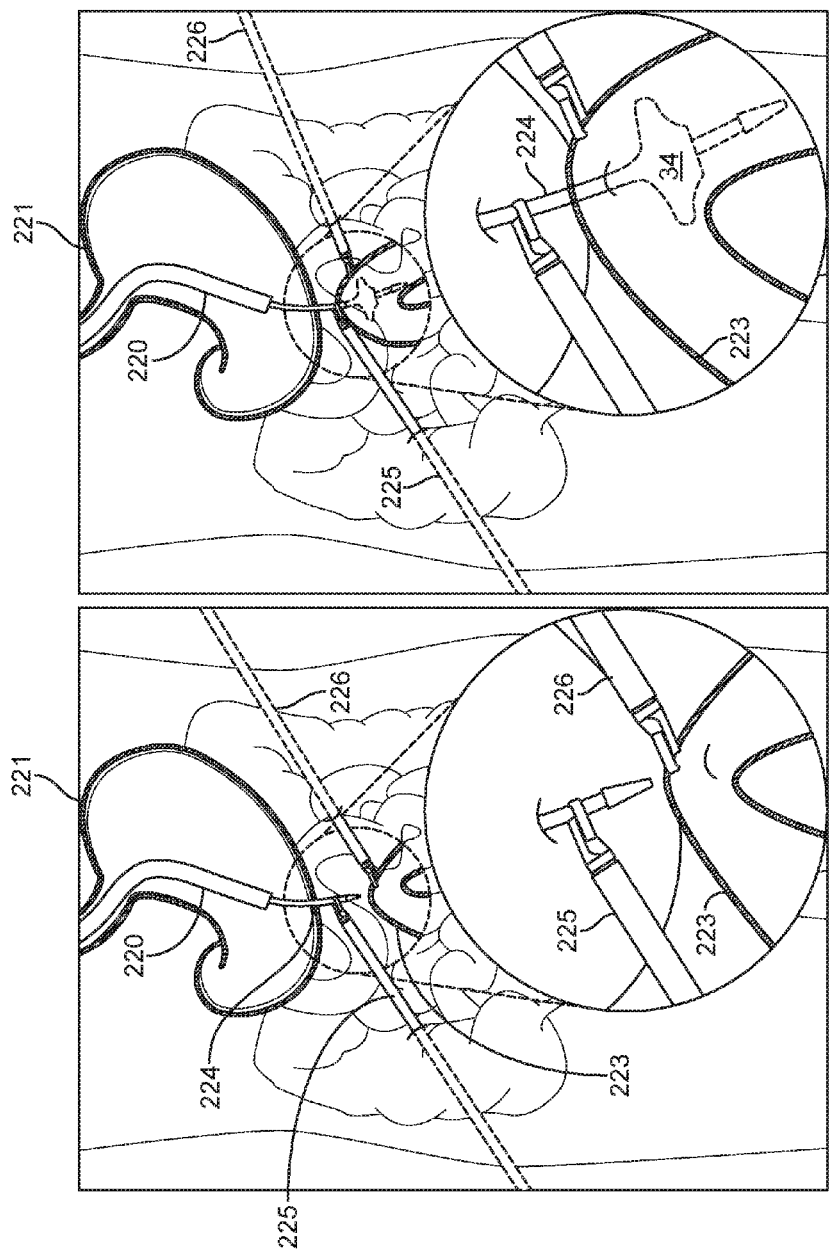

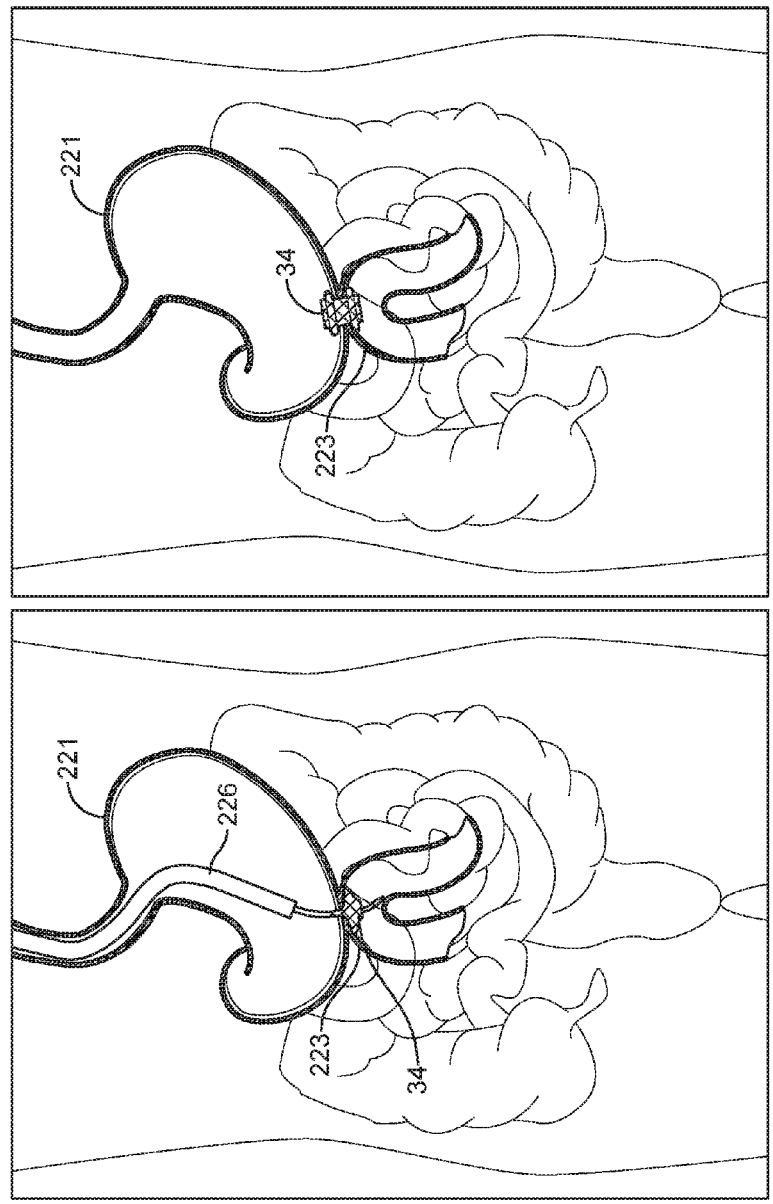

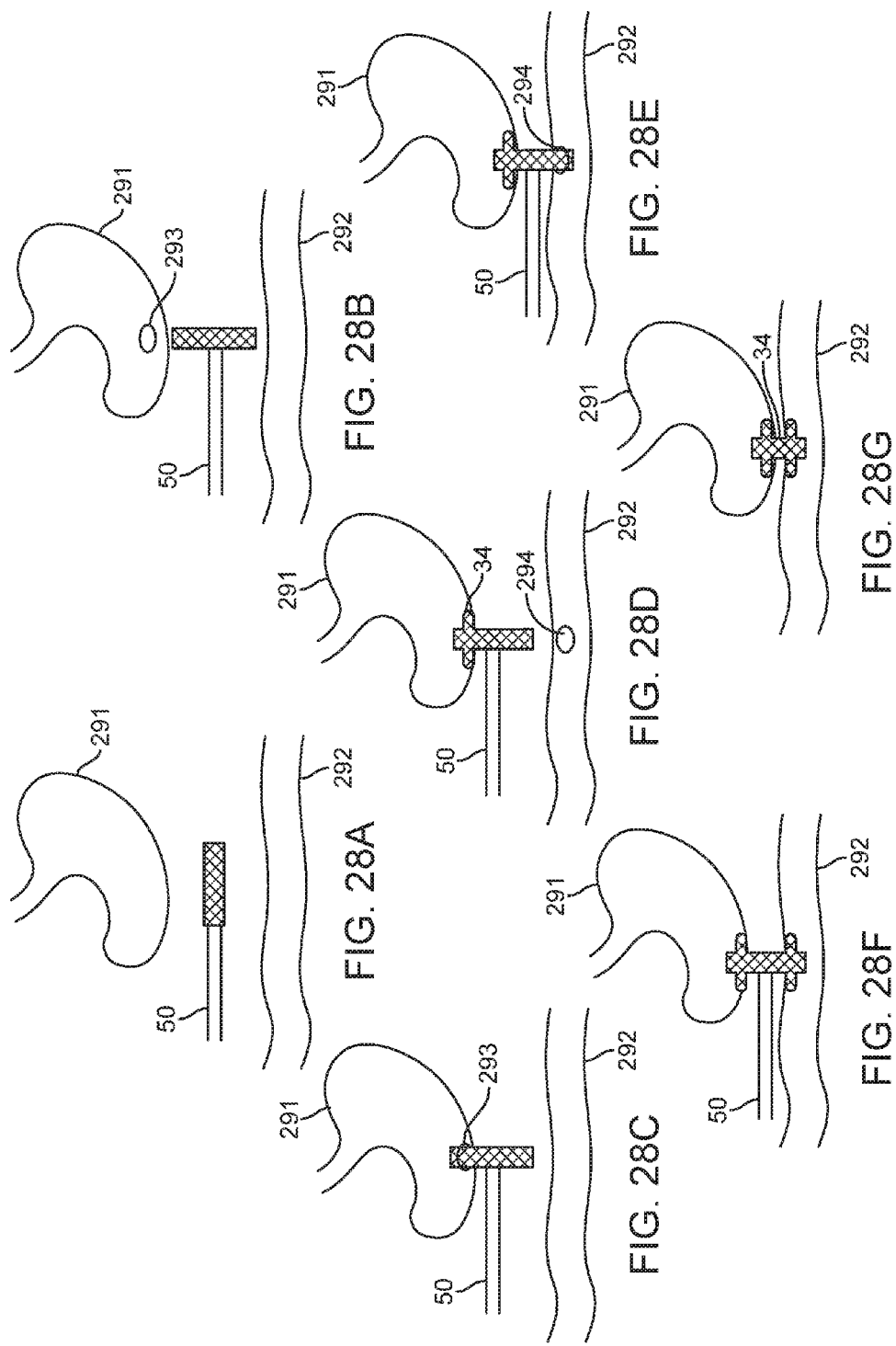

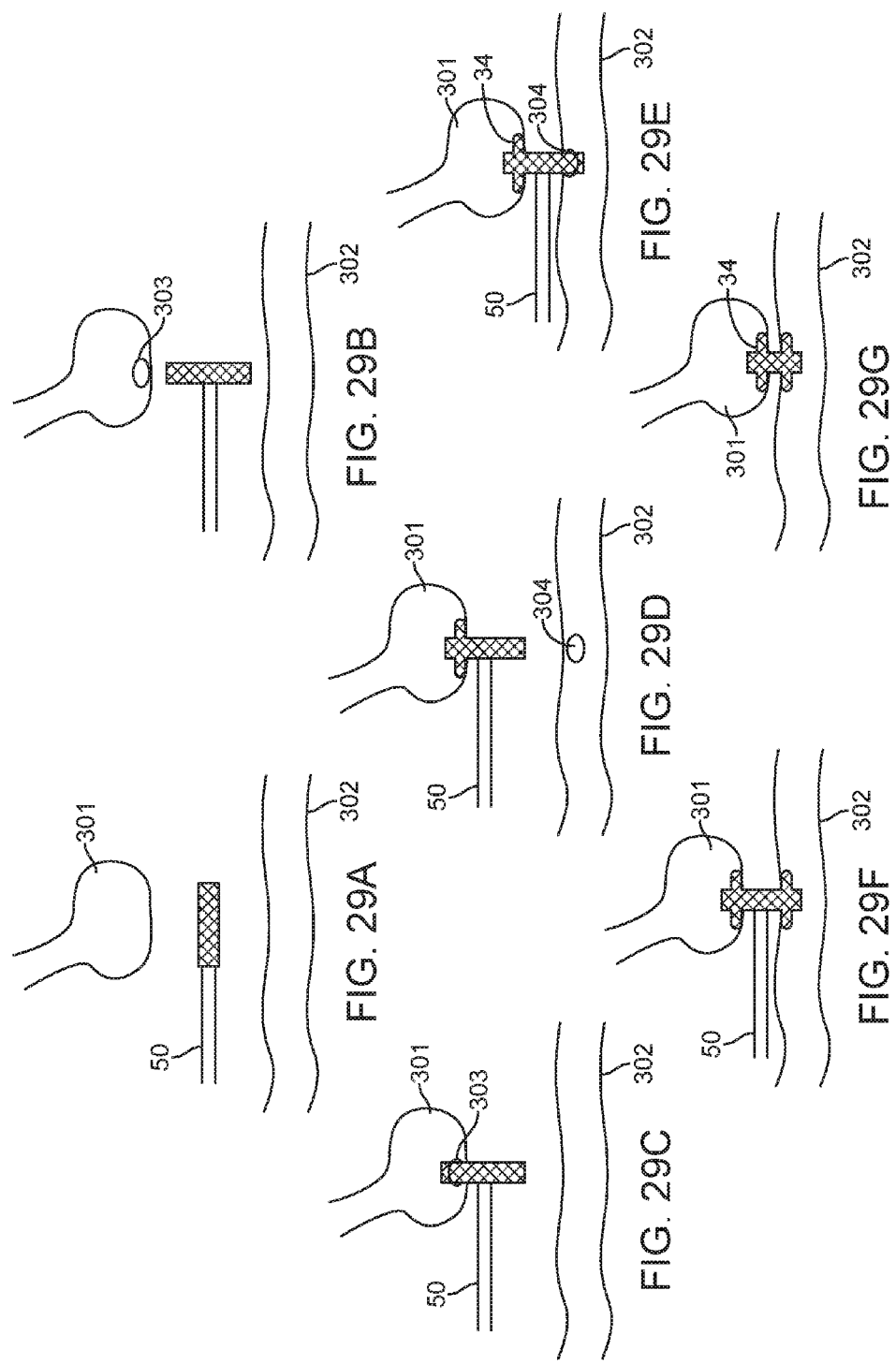

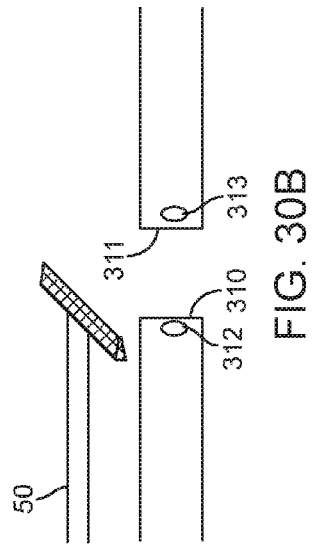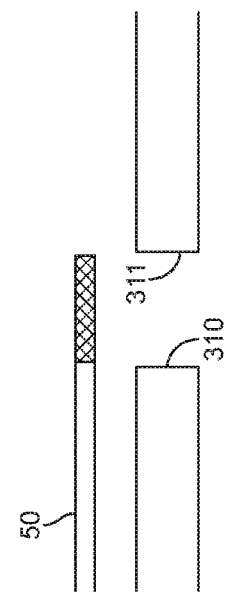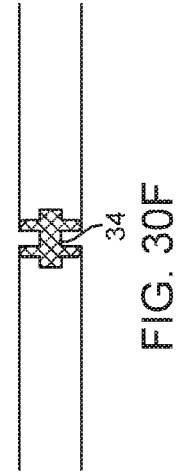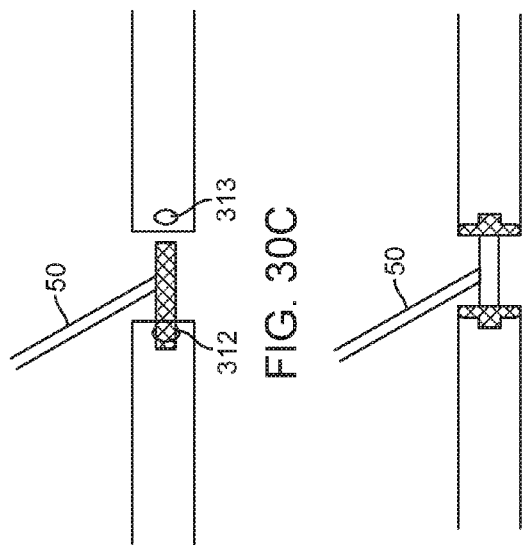

DEVICES AND METHODS FOR FORMING AN ANASTOMOSIS

CROSS-REFERENCE TO RELATED APPLICATION

This application is a continuation of U.S. patent application Ser. No. 14/186,994, filed Feb. 21, 2014; which claims priority to U.S. Provisional Application No. 61/767,577 filed on Feb. 21, 2013 titled "Devices and Methods for Forming an Anastomosis", the disclosures of which are incorporated by reference herein in their entirety.

This application is related to U.S. Provisional Application No. 61/648,544 filed on May 17, 2012 and U.S. Provisional Application No. 61/727,629 filed on Nov. 16, 2012, the disclosures of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates generally to medical methods and apparatus. More particularly, the present disclosure relates to methods and apparatus for forming an anastomosis between bodily tissues and organs.

BACKGROUND

The present disclosure relates generally to medical methods and apparatus. More particularly, the present disclosures relates to methods and apparatus for forming an anastomosis.

A number of medical procedures require forming an anastomosis between adjacent body lumens. For example, a number of procedures may be performed by entering the gastrointestinal (GI) tract through a first organ or structure, such as the esophagus, stomach, duodenum, small intestine, large intestine, or peritoneal cavity, and delivering the anchor or stent to adjacent organs and lumen or tissue structures such as an adjacent portion of the GI tract, the bile duct, the pancreatic duct, the gallbladder, the pancreas, cysts, pseudocysts, abscesses, and the like. Such methods and apparatus can also be used for access to and from portions of the urinary tract, such as the urinary bladder and ureter, the pulmonary tract, such as the trachea and bronchi, and the biliary tract, such as the bile duct and gallbladder, and vascular applications, as well.

Stents are commonly used to facilitate the opening of closed vessels for access, drainage or other purposes. Tissue anchors are used to secure adjacent tissues or organs. Inter-luminal tissue anchors, which include a central lumen, are used to facilitate fluid communication between adjacent ducts, organs or lumens. Often, the precise placement of the tissue anchor or stent is necessary, especially when the tissue anchor or stent has well defined anchoring elements at the proximal and/or distal ends, and the device is used to secure adjacent lumens.

When deploying a stent or other tissue anchor between adjacent body lumens, organs, or other structures, it is typically necessary to penetrate both a wall of the first body lumen through which access is established and a wall of a second body lumen which is the target for the procedure. When initially forming such access penetrations, there is a significant risk of leakage from either or both of the access body lumen and the target body lumen into the surrounding space including, but not limited to the peritoneal cavity. In some procedures, such as those involving bariatric, transgastric, or transduodenal bile duct access, loss of body fluid into surrounding tissues and body cavities can present a substantial risk to the patient. The risk can be exacerbated when it is necessary to not only penetrate the luminal walls to gain initial access, usually with a needle, but to subsequently enlarge or dilate the initial penetration.

Gastric bypass surgery has become more common recently with laparoscopic surgery. One type of gastric bypass surgery is Roux-en-Y (RNY) gastric bypass surgery. In bariatric bypass surgery fluid leakage from the surgical anastomosis site is a concern amongst physicians. With surgeries such as the Roux-en Y Gastric Bypass, physicians are required to surgically create and affix two such anastomoses; one at the gastric Fundal pouch to the Jejunum, and one at the Ileum to Duodenum. FIGS. 1A-1C illustrates examples of the RNY surgery. The surgery involves cutting a portion of the stomach 1 to create a gastric/fundal pouch 5 at cut line 4. The hole created in the stomach is sealed off with staples 7. The intestines are cut between the duodenum 2 and jejunum 3 at cut line 4. Food will then bypasses the sealed off portion of the stomach 6. The gastric or fundal pouch 5 is then connected to the jejunum 3. The duodenum 2 is then attached to the ileum/jejunum 4 to form an anastomosis 9 downstream of the anastomosis between the gastric pouch and jejunum 8. After the RNY surgery food flows down the esophagus into the gastric pouch. The gastric pouch has a smaller volume than the patient's previous stomach. Food bypasses the old volume of the stomach. Digestive juices meet the food in the jejunum instead of mixing with the food in the bypassed portion of the patient's stomach. FIG. 1C illustrates digestive juices flowing from the gallbladder 10a through the cystic duct and common hepatic duct into the duodenum 2. FIG. 1C also illustrates digestive juices flowing from the pancreas 10b through the pancreatic duct into the duodenum 2.

RNY surgery is believed to be effective because the new stomach (gastric pouch) is small and cannot accommodate the same volume of food as the patient's old stomach. If the patient eats too much they will throw up. It is possible to stretch the new gastric pouch but it is difficult. It is also theorized that the surgery can change the satiation response/pattern in the patient. For example, it is possible that the presence of food and digestive juices in the jejunum could send a signal to the body that the patient is full. The RNY surgery also decreases retention time of the food with the digestive juices because the digestive juices no longer mix with food in the stomach and instead mix downstream of the gastric pouch within the jejunum. The decreased retention time between the food and digestive juices can also have an effect on adsorption of calories and nutrients.

It is important to form a tight anastomosis between the gastric pouch and jejunum as well as between the duodenum and jejunum. Patient recovery times are typically around 5 days for RNY surgery. Leakage can cause severe complications in the patient after surgery. Leakage occurs in about 20% of patients. If there is leakage at either of the anastomosis sites then the hospital stay is much longer, on average about 25 days. In current RNY surgery staples are typically used to the seal off the bypassed stomach area, to create the gastric fundal pouch, and to create anastomoses. However, the stapling process can be lengthy using laparoscopic procedures and the diameter of the anastomoses formed from stapling vary between patients and doctors.

Other complications can also occur, such as the formation of a stricture at the anastomosis site. The stricture can cause the formation of thicker walls at the anastomosis site thereby decreasing the internal diameter of the passage. The decreased diameter can restrict the flow of food through the anastomosis site.

Colon resection surgery is another surgery that involves forming an anastomosis with the intestines. A section of the intestines can be removed and the cut ends of the intestines are connected by an anastomosis as shown in FIG. 2A. The anastomosis can be created by stapling the cut ends of the intestines together (FIG. 2A-2C). Endolinear connectors can also be attached and used to connect the cut ends of the intestines. Typically the endolinear connectors have a reduced diameter and can restrict flow of non-liquid material through the anastomosis.

It is desirable to provide improved protocols and access tools for forming an anastomosis while minimizing the risk of leakage. Quicker methods for forming anastomoses are also desired.

SUMMARY OF THE DISCLOSURE

The present invention relates to improved stents for forming an anastomosis within the digestive tract, laparoscopic and endoscopic tools for delivering stents, and methods for forming an anastomosis using the stents and tools described herein.

Stents are disclosed herein. In some embodiments the stents include a stent body formed of a woven filament braid having a constrained configuration, the stent body having an expanded configuration with a proximal end of the body expanded into a proximal flange, a distal end of the body expanded into a distal flange, and a cylindrical region between the proximal and distal flanges. At least the cylindrical region of the stent is covered. The covered cylindrical region has an open interior passage configured to permit the flow of fluid, digested food, and partially digested food therethrough. The proximal and distal flanges are configured to permit the flow of fluid, digested food, and partially digested food therethrough. The proximal and distal flanges are configured to atraumatically engage bodily tissue between the proximal flange and distal flange with the proximal and distal flanges each having a pull-out force of greater than about 2.94 N. The stent is also configured to be retrievable through a catheter device from the expanded configuration.

In any of the embodiments disclosed herein the stent can include a proximal flange plug configured to block food from getting stuck in an interior area of the proximal flange and a distal flange plug configured to block food from getting stuck in an interior area of the distal flange. In any of the embodiments disclosed herein the stent includes an interior diameter of the proximal flange plug and an interior diameter of the distal flange plug are substantially the same as an interior diameter of the cylindrical region. In any of the embodiments disclosed herein the stent has a proximal flange including a double-walled flange and the distal flange includes a double-walled flange.

In any of the embodiments disclosed herein the stent has a proximal flange and distal flange each comprising five or more inflection points. In any of the embodiments disclosed herein the stent has a proximal flange and distal flange each including six or more inflection points.

In any of the embodiments disclosed herein the stent has a proximal flange including a curled wall that curls towards the open interior passage of the stent and a distal flange including a curled wall that curls towards the open interior passage of the stent.

In any of the embodiments disclosed herein the stent has a proximal flange including a curled wall that curls towards an exterior of the covered cylindrical region and a distal flange including a curled wall that curls towards an exterior of the covered cylindrical region.

In any of the embodiments disclosed herein the stent includes a proximal flange configured to bend over the covered cylindrical region and the distal flange is configured to bend over the covered cylindrical region. In any of the embodiments disclosed herein the stents include a proximal flange further comprising a curved surface adjacent to the proximal end of the proximal flange configured to atraumatically engage the bodily tissue and a distal flange further comprising a curved surface adjacent to the distal end of the distal flange configured to atraumatically engage the bodily tissue.

In any of the embodiments disclosed herein the stents have a proximal flange with an interior diameter greater than a diameter of the covered cylindrical region and a distal flange with an interior diameter greater than the diameter of the covered cylindrical region.

In any of the embodiments disclosed herein the entire stent body is covered.

In any of the embodiments disclosed herein the stent is a self-expanding stent.

Self-expanding anastomotic stents are disclosed herein. In any of the embodiments disclosed herein the self-expanding stents include a flexible body having an unexpanded configuration and an expanded configuration, the expanded configuration including a proximal end of the body expanded into a proximal flange, a distal end of the body expanded into a distal flange, and a cylindrical region between the proximal and distal flanges. At least the cylindrical region is covered. The covered cylindrical region has an open interior passage configured to permit the flow of fluid, digested food, and partially digested food therethrough. The proximal and distal flanges each projecting away from the interior passage of the cylindrical region to permit the flow of fluid, digested food, and partially digested food therethrough. The stent is also configured to be retrievable from the expanded configuration within a patient after formation of an anastomosis.

In any of the embodiments disclosed herein the proximal and distal flanges are configured to atraumatically engage bodily tissue with the proximal flange and distal flange each having a pull-out force of greater than about 2.94 N.

In any of the embodiments disclosed herein the proximal flange and distal flange each comprise five or more inflection points. In any of the embodiments disclosed herein the proximal flange and distal flange each include six or more inflection points.

In any of the embodiments disclosed herein the proximal flange includes a curled wall that curls towards an exterior of the covered cylindrical region and the distal flange includes a curled wall that curls towards an exterior of the covered cylindrical region.

In any of the embodiments disclosed herein the proximal flange is configured to bend over the covered cylindrical region and the proximal flange is configured to bend over the covered cylindrical region.

In any of the embodiments disclosed herein the proximal flange further comprises a curved surface adjacent to the proximal end of the proximal flange configured to atraumatically engage the bodily tissue and the distal flange further comprises a curved surface adjacent to the distal end of the distal flange configured to atraumatically engage the bodily tissue.

Medical tools configured for laparoscopic use are disclosed herein. The medical tools can include a handle, a shaft engaged with the handle, a self-expanding stent, and a stent holder configured to hold the self-expanding stent in a constrained position. The stent holder includes a material restraining the self-expanding stent with the material configured to hold the stent in the constrained position, configured to open to allow the stent to expand, and configured to be removable after deployment of the stent.

In any of the embodiments disclosed herein the medical tools can include an articulating element configured to change the orientation of the stent holder relative to the shaft from a first orientation in line with an axial plane defined by the shaft to a second orientation to the axial plane defined by the shaft.

In any of the embodiments disclosed herein the stent holder is configured to selectively release a first end of the stent and a second end of the stent.

In any of the embodiments disclosed herein the medical tools can include a first pull wire assembly configured to controllably release the first end of the stent by opening the flexible material and a second pull wire assembly configured to controllably release the material constraining the second end of the stent by opening the flexible material.

In any of the embodiments disclosed herein the stent holder and self-expanding stent is part of a removable cartridge assembly.

In any of the embodiments disclosed herein the medical tools can include a sharpened distal point configured to penetrate bodily tissue.

Methods for forming an anastomosis are disclosed herein. The methods can include endoscopically accessing a stomach of a patient with an endoscope and a catheter device carrying a stent, making an incision in a wall of the stomach; advancing the endoscope and catheter device through the incision in the wall of the stomach, advancing the endoscope to a location in a peritoneal cavity adjacent to a target location in an intestine, advancing the catheter device through a wall of the intestines, deploying a first end of the stent in the intestines, and deploying a second end of the stent in the stomach to form a pathway between the stomach and intestines.

In any of the embodiments disclosed herein the target location in the intestines is a jejunum or ileum.

In any of the embodiments disclosed herein the target location in the intestines is a duodenum.

In any of the embodiments disclosed herein the stomach is a fundal pouch formed during a gastric bypass procedure. In any of the embodiments disclosed herein, the methods include forming the fundal pouch as part of a gastric bypass procedure before endoscopically accessing the GI tract with the catheter device. In any of the embodiments disclosed herein, the methods include after deploying the first end of the stent pulling proximally on the catheter device and first end of the stent to engage the first end of the stent with the wall of the intestines to move the intestines in apposition with the fundal pouch wall.

In any of the embodiments disclosed herein the stent is a self-expanding stent including a first double-walled flange structure on the first end and a second double-walled flange structure on the second end.

In any of the embodiments disclosed herein penetrating a wall of the ileum or jejunum further comprises activating an energized portion adjacent to the tip of the catheter device, contacting the jejunum or ileum wall with the energized tip, and advancing the energized tip through the jejunum or ileum wall.

In any of the embodiments disclosed herein deploying the stent includes withdrawing a sheath restraining the stent and self-expanding the stent.

In any of the embodiments disclosed herein after deploying the first end of the stent in the jejunum or ileum further comprises pausing withdrawal of the sheath after deploying the first end of the stent in the jejunum or ileum and verifying deployment of the first end within the jejunum or ileum. In any of the embodiments disclosed herein after verifying deployment of the first end of the stent within the jejunum or ileum continuing the withdrawal of the sheath to deploy the second end of the stent within the stomach.

In any of the embodiments disclosed herein the methods further comprise removing the stent after formation of the anastomosis.

In any of the embodiments disclosed herein prior to endoscopically accessing the fundal pouch of the patient with the catheter device carrying the stent, further comprising: laparoscopically accessing a peritoneal cavity; creating a laparoscopic environment within the peritoneal cavity; and introducing a hand tool to the peritoneal cavity. In any of the embodiments disclosed herein the methods further comprise guiding a tip of the catheter device into the peritoneal cavity using the hand tool and guiding the tip of the catheter device through the peritoneal cavity to the target location outside of the jejunum using the hand tool. In any of the embodiments disclosed herein the methods further comprise holding the jejunum adjacent to the target location in the jejunum with a second hand tool in the peritoneal cavity prior to penetrating the jejunum wall. In any of the embodiments disclosed herein the methods further comprise visualizing from the peritoneum the fundal pouch, a tip of the catheter device, and target location in the jejunum using laparoscopic guidance.

In any of the embodiments disclosed herein after forming the fundal pouch further comprising: stitching a portion of the fundal pouch to a portion of the jejunum or ileum adjacent to the target location of the jejunum or ileum.

In any of the embodiments disclosed herein advancing the catheter device through a wall of the intestines further comprises advancing a grasper device from a port in the endoscope, grasping the intestines adjacent to the target location with the grasper device, and advancing the catheter device through the wall of the intestines while grasping the intestines with the grasper device.

Methods for forming an anastomosis are disclosed. The methods can include endoscopically accessing a stomach of a patient with a catheter device carrying a stent, delivering a position marker visible under ultrasonic guidance to a target location in the intestines, ultrasonically locating the position marker in the target location in the intestines relative to the catheter device carrying the stent, advancing the catheter device to penetrate a wall of the stomach and a wall of the intestines, deploying a first end of the stent in the intestines, and deploying a second end of the stent in the stomach to form a pathway between the stomach and intestines. In some embodiments the target location in the intestines is the jejunum or ileum.

Methods for forming an anastomosis are disclosed herein. The methods can include deploying a stent within a passage between a fundal pouch, formed during a gastric bypass procedure, and an intestine.

In any of the embodiments disclosed herein the methods further comprise forming a fundal pouch during the gastric bypass procedure and connecting the fundal pouch to an intestines to form the passage between the fundal pouch and intestines.

In any of the embodiments disclosed herein the methods further comprise removing the stent after formation of the anastomosis.

In any of the embodiments disclosed herein deploying the stent further comprises deploying a first end of the stent within the intestines and deploying a second end of the stent in the fundal pouch.

Methods for forming an anastomosis are disclosed herein. The methods include accessing a peritoneal cavity of a patient with a laparoscopic device comprising a stent having a first end and second end, penetrating a wall of a fundal pouch with the laparoscopic device, deploying a first end of the stent in the fundal pouch, penetrating a wall of the jejunum with the laparoscopic device, and deploying a second end of the stent in the jejunum to form a pathway between the fundal pouch and jejunum.

In any of the embodiments disclosed herein the methods further comprise forming a fundal pouch as part of a gastric bypass procedure before accessing the peritoneal cavity of the patient with the laparoscopic device.

In any of the embodiments disclosed herein after deploying the first end of the stent, pulling traction on the laparoscopic device to engage a first flange on the first end of the stent with the wall of the fundal pouch.

In any of the embodiments disclosed herein the stent is a self-expanding stent including a first double-walled flange structure on the first end and a second double-walled flange structure on the second end.

In any of the embodiments disclosed herein deploying the stent comprises removing a restraint from the stent and allowing the stent to self-expand. In any of the embodiments disclosed herein removing the restraint includes withdrawing a sheath. In any of the embodiments disclosed herein removing the restraint includes removing a material restraining the stent.

In any of the embodiments disclosed herein the methods further comprise removing the stent endoscopically after formation of the anastomosis.

In any of the embodiments disclosed herein the methods further comprise after accessing the peritoneal cavity and before penetrating the wall of the fundal pouch, rotating the orientation of a stent holder holding the stent relative to a shaft of the laparoscopic device from a first orientation in line with an axial plane defined by the shaft to a second orientation relative to the axial plane defined by the shaft.

Methods for forming an anastomosis in a digestive tract of a patient are disclosed herein. The methods include accessing a peritoneal cavity of the patient with a laparoscopic device carrying an anastomotic device, penetrating a first intestinal wall adjacent to a first closed end of the intestines with a surgical device in the peritoneal cavity, placing a first end of the anastomotic device in the penetration in the first intestinal wall, deploying the first end of the anastomotic device within a first internal volume of the intestines adjacent to the penetration in the first intestinal wall, penetrating a second intestinal wall adjacent to a second closed end of the intestines with the surgical device in the peritoneal cavity, placing a second end of the anastomotic device in the penetration in the second intestinal wall; and deploying the second end of the anastomotic device within a second internal volume of the intestines adjacent to the penetration in the second intestinal wall thereby forming a pathway between the first internal volume of the intestines and the second internal volume of the intestines.

In any of the embodiments disclosed herein the first closed end of the intestines is a first closed portion of a colon and the second closed end of the intestines is a second closed portion of the colon.

In any of the embodiments disclosed herein the anastomotic device is a stent. In any of the embodiments disclosed herein deploying the first end of the stent further comprises after deploying the first end of the stent within the first internal volume of the intestines, pulling traction on a double-walled flange structure of the stent to engage the first end of the stent with first intestinal wall and to move the first intestinal wall closer to the penetration in the second intestinal wall.

In any of the embodiments disclosed herein the anastomotic device includes two separate pieces, the first end including a first piece comprising a first tissue engagement structure and a first magnetic coupling structure, the second end including a second piece comprising a second tissue engagement structure and a second magnetic coupling structure. In any of the embodiments disclosed herein the methods further comprise magnetically connecting the first magnetic coupling structure to the second magnetic coupling structure.

In any of the embodiments disclosed herein the methods further comprise endoscopically removing the anastomotic device after formation of an anastomosis.

Methods for forming an anastomosis in a digestive tract of a patient are disclosed herein. The methods include accessing a first portion of the intestines with a catheter device carrying a stent, penetrating a wall of the first portion of the intestines adjacent to a first closed end of the intestines with the catheter device, penetrating a wall of a second portion of the intestines adjacent to a second closed end of the intestines with the catheter device, deploying a first end of the stent such that it engages with the wall of the second portion of the intestines, and deploying a second end of the stent such that it engages with the wall of the first portion of the intestines thereby forming a pathway between the first portion of the intestines and the second portion of the intestines.

In any of the embodiments disclosed herein the first portion of the intestines is a first portion of the colon and the second portion of the intestines is a second portion of the colon.

In any of the embodiments disclosed herein accessing the first portion of the intestines with the catheter device further comprising accessing the peritoneal cavity with the catheter device, forming a penetration in the first portion of the intestines, and advancing the catheter into an internal volume of the first portion of the intestines.

In any of the embodiments disclosed herein the first end of the stent has a double-walled flange structure and the second end of the stent has a double-walled flange structure and the method further comprises pulling traction on the double-walled flange structure of the first end of the stent to engage the first end of the stent with the wall of the second portion of the intestines and pulls the second portion of the intestines in apposition with wall of the first portion of the intestines.

In any of the embodiments disclosed herein penetrating the wall of the first portion of the intestines and penetrating the wall of the second portion of the intestines includes electrically energizing a tip of the catheter device and contacting the wall of the first portion of the intestines and the wall of the second portion of the intestines with the electrically energized tip.

In any of the embodiments disclosed herein the methods further comprise using a laparoscopic tool to guide the catheter device prior to penetrating the wall of the second portion of the intestines.

In any of the embodiments disclosed herein the methods further comprise removing the anastomotic device after formation of an anastomosis.

BRIEF DESCRIPTION OF THE DRAWINGS

FIGS. 3A-3D illustrate a catheter device in accordance with some embodiments.

FIGS. 13A-13C illustrate a laparoscopic surgical device in accordance with some embodiments.

FIGS. 15A-15G illustrate cross sections of stents in accordance with some embodiments.

FIGS. 16A-16J illustrate cross sections of stents in accordance with some embodiments.

FIGS. 20A-20C illustrate a method for deploying a stent between a stomach and a portion of the intestines in accordance with some embodiments.

FIGS. 21A-21D illustrate a method for deploying a stent between a stomach and a portion of the intestines using ultrasound guidance in accordance with some embodiments.

FIGS. 22A-22D illustrate a method for deploying a stent between a stomach and a portion of the intestines using an endoscopic catheter and laparoscopic tools in accordance with some embodiments.

FIGS. 28A-28G illustrate a laparoscopic method for deploying a stent between a stomach and a portion of the intestines in accordance with some embodiments.

FIGS. 29A-29G illustrate a laparoscopic method for deploying a stent between a fundal pouch and a portion of the intestines in accordance with some embodiments.

FIGS. 30A-30F illustrate a laparoscopic method for deploying a stent between two sealed off sections of the intestines in accordance with some embodiments.

DETAILED DESCRIPTION

Figure 1A:
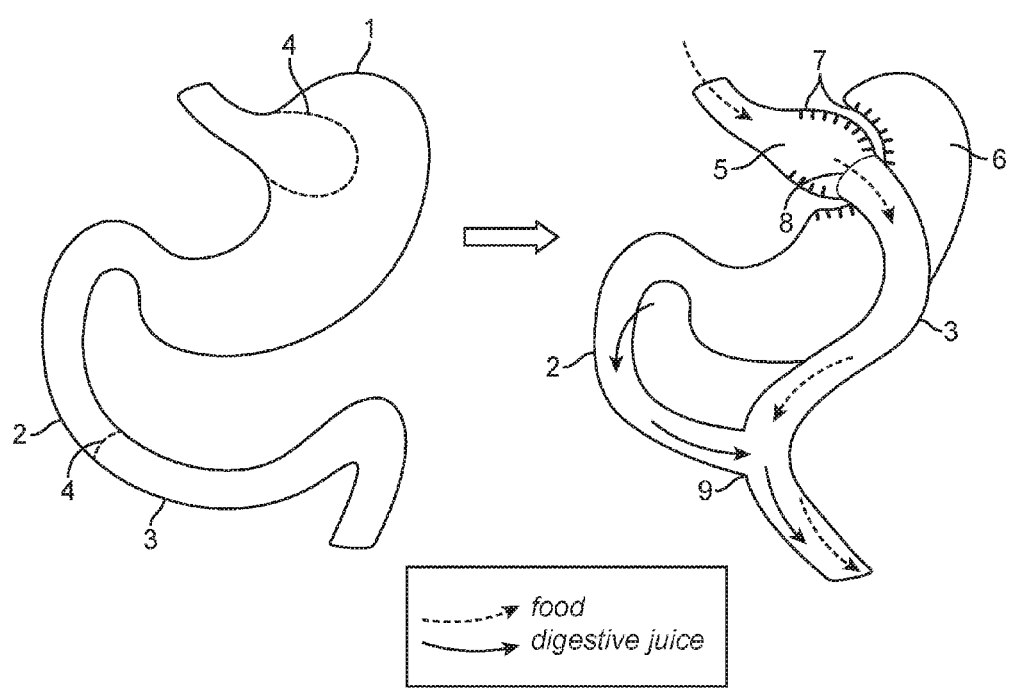
FIGS. 1A-1C illustrate schematic examples of gastric bypass surgery.
Figure 1B:
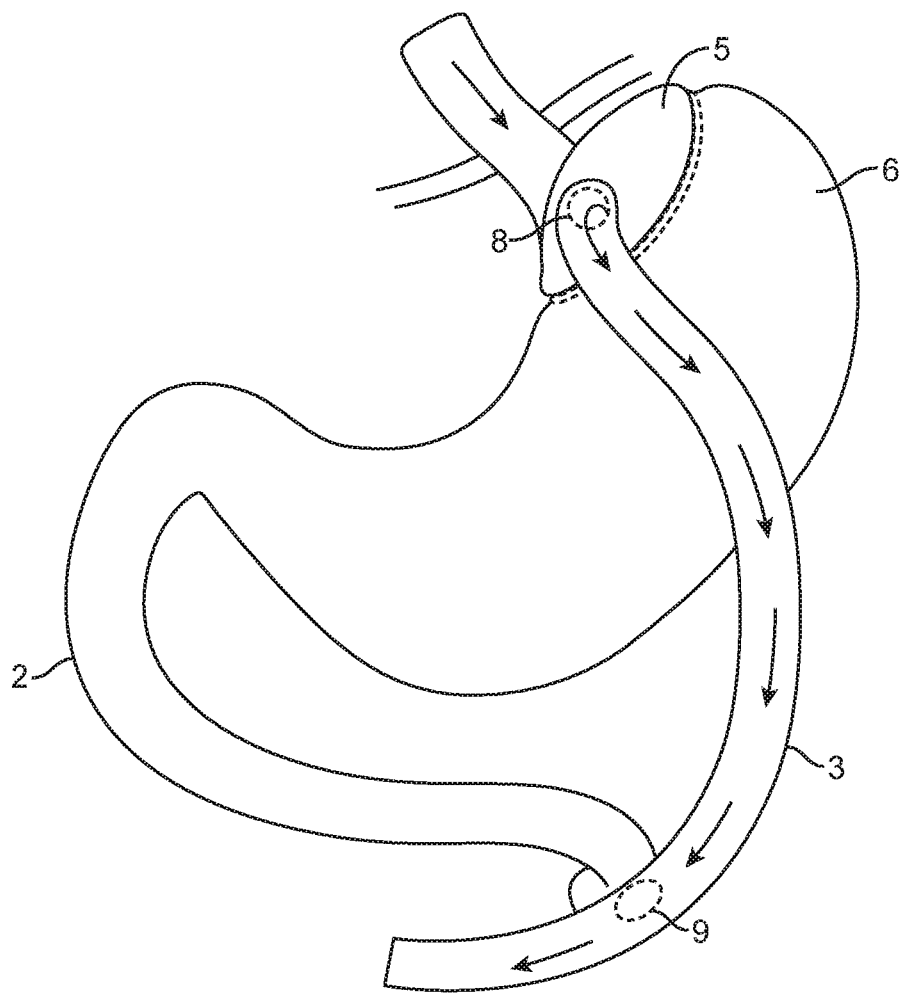
Figure 1C:
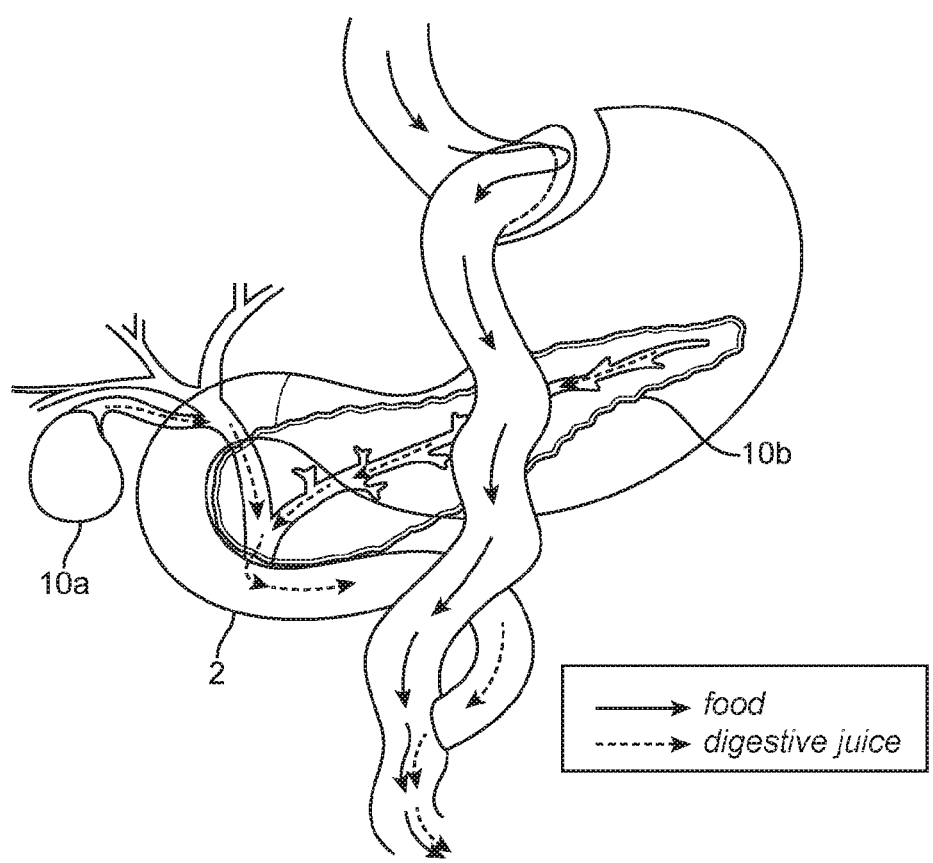

Methods and devices are disclosed herein for forming an anastomosis. The devices and methods disclosed herein can be used to form multiple anastomoses. Tissue anchors and stents can be used to form the anastomosis. The anastomosis can be made using an endoscope, catheter, laparoscopic surgical instrument, laparoscopic, general surgery device, or a combination of one or more of these devices. The stents disclosed herein can be delivered using catheter based systems. In some embodiments the stents disclosed herein can be delivered using a laparoscopic device. In some embodiments the stents disclosed herein can be delivered using a rigid catheterless system. In some embodiments the stents can be delivered using a combination of a catheter and laparoscopic tools, for example the stent can be deployed with the catheter device and navigation and visualization assistance can be provided by the laparoscopic tools.

Improved access tools, improved stent designs to form consistent leak free anastomosis having a known size without blocking food flow, and methods for deploying the stents endoscopically and laparoscopically are disclosed herein. The devices and methods disclosed herein are useful for forming a consistent leak-free anastomosis between body lumens. The ability to form a leak-free anastomosis with a consistently sized fluid pathway is alternatively advantageous for applications where the surgeon or doctor has previously connected two tissues using manual methods with staples and sutures, for example as done in gastric bypass surgeries. The stents disclosed herein can be deployed in the anastomoses formed between the fundal pouch and jejunum and duodenum to ileum to promote formation of a healthy anastomosis further reduce the risk of leakage of material in to the peritoneal cavity. The stents can also be used to form a pathway between the stomach or fundal pouch and a portion of the intestines such as the jejunum.

Benefits are also applicable to procedures forming an anastomosis between any two portions of the intestines, such as the closed ends in a colon resection procedure. The prior art methods typically form a stapled or sutured connection that forms a stricture having a reduced diameter that can decrease the flow rate of material through the intestines. The stents disclosed herein can be used to form an anastomosis between two closed off portions of the intestines with an improved capacity for the flow of material through the anastomosis as compared to convention colon resection techniques.

Although discussed in detail with reference to forming anastomoses between adjacent body lumens in the gastro intestinal tract, such as between a stomach and portion of the intestines and between two portions of the intestines, the methods and devices can be used herein for forming any surgical anastomosis.

In a roux-en-y procedure the stents disclosed herein can be used at the two surgical anastomosis sites, one at the gastric Fundal pouch to intestines, e.g. jejunum and additionally between two portions of the intestines, such as at the Duodenum to Ileum connection. More broadly the stents can be used to join any segment of the GI tract. In some embodiments the stents and tissue anchors can be used for any type of surgical anastomosis between tissue planes.

The tissue anchors and stents disclosed herein can be delivered using catheter based delivery systems in some embodiments. Catheter based devices and methods for placing stents are disclosed in co-owned U.S. Pat. No. 8,357,193 and U.S. Patent Publication No. 2013-0310833. A natural orifice can be used for access to the target location or the catheter can be introduced into the intestines through the peritoneal cavity and into the intestines. In another example the catheter can be introduced into any body lumen associated with a NOTES procedure, such as the bile duct, gallbladder, etc. The catheter based delivery systems can attach to an endoscope or other similar device for navigation. The catheter devices can be used with laparoscopic tools to improve visualization and positioning of the device.

A needle can be used for initial access to the targeted region followed by guidewire access for the catheter to the targeted region. In some cases the catheter device can be used to directly access the target location without a guidewire or needle. Using the catheter device without a guidewire can be referred to as freestyle access. The catheter can also be guided by laparoscopic tools as described herein.

FIGS. 3A-3D illustrate a catheter device 11 in accordance with some embodiments for deploying a stent between body lumens. The catheter device 11 of FIG. 3A includes a control handle 12 having a body 14 with a first slide actuator 15 with knob 16 and lock 20. A second slide actuator 18 with lock 22, scope locking mechanism 24, electrical plug 23, catheter body 26, a sheath 27, shaft 28, stent friction material 30, distal tapered tip 32 and stent or other tissue anchor 34 (FIG. 3BA). FIG. 3B is an enlarged portion of the end of the device 11, including the distal tapered tip 32.

The distal tapered tip 32 includes a distal tip base 33. The sheath 27 can contact the distal tapered tip and engage with an outer diameter of the distal tip base 33. The sheath 27 can radially constrain the stent 34 and prevent the stent 34 from expanding. The distal tapered tip 32 can include a conductive portion with a cutting element 35. The illustrated cutting element 35 has a concentric design about a guidewire lumen 39. The conductive projections 36 extend from the cutting element 35 towards the outer diameter of the distal tip 32. The illustrated projections 36 enter into a recessed portion 41 (FIG. 3D) of the distal tip 32. In some embodiments the conductive cutting element is optional. For example the catheter can include a blunt or cone shaped tip without a conductive cutting element in any of the methods described herein.

The conductive areas of the tip, such as the cutting element 35 and projections 36 can be configured to cut, heat, and/or cauterize tissue in a patient. Electrical energy is supplied to energize the conductive areas of the tip. Electrical energy can be supplied to the conductive portions of the tip, such as radiofrequency (RF) and high-frequency (HF) energy. The electrical energy can be supplied through electrical plug 23. The handle includes an electrical control to control the electrical energy supplied to the tip.

The cutting element 35 and illustrated projections 36 can be made out of a conductive medical grade material that is biocompatible, such as stainless steel. A different conductive material, such as copper, can be used to supply electrical energy to the cutting element 35 and projections 36. The projections 36 can connect to the wiring 38 at connection 37. The wiring 38 is in electrical contact with the electrical plug 23. The electrical plug 23 supplies electrical energy through the wiring 38 to the cutting element 35 and projections 36. The distal tip 32 is made out of an insulating material to insulate the cutting element 35 and projections 36 from the surrounding device structure.

FIGS. 3C-3D illustrate enlarged views of the distal tip 32. FIG. 3C is a side view showing the projections 36 entering the distal tip 32 just short of the outer diameter of the distal tip 32. FIG. 3D is a top view of the distal tip 32 showing the projections 36 entering into the recessed portion 41 of the distal tip 32. The distal tip shown in FIGS. 3C-3D can produce a tissue cut pattern that contains a central cut region with two linear cuts protruding radially from the central region or ring. The projections 36 in FIGS. 3A-3C recede into the recessed portion 41 of the distal tip 32 before the distal tip 32 reaches its maximum diameter. In some embodiments the projections can be covered adjacent to the outer diameter such that the exposed portion of the projections do not reach the maximum outer diameter of the distal tip 32. The slits made in the tissue by the projections 36 are slightly shorter than the diameter of the tip. Some force can be applied to push the distal tip through the tissue slits made by the energized tip. The elasticity of the tissue can accommodate the slightly larger diameter of the distal tip and catheter. The tight fit can prevent leakage of biological material from the body lumen.

The tip designs disclosed herein allow for an increased electrical current density that can facilitate quicker cutting through tissue and reduced trauma to the surrounding tissue areas than conventional blunt nose conical tips having a welded electrical connections, such as those produced by Cook Medical Inc. The tip produced by Cook Medical provides electrical power to the entire blunt tip. The tip requires a relatively large amount of power and carries a lower electrical current density. The lower electrical current density requires longer times to cut through tissue, which can produce excessive heating that can cause damage to the surrounding tissue areas and the surrounding catheter parts. The blunt nose can also cause tearing of the tissue, which increases the chances of leakage of biological material.

Figure 4A:
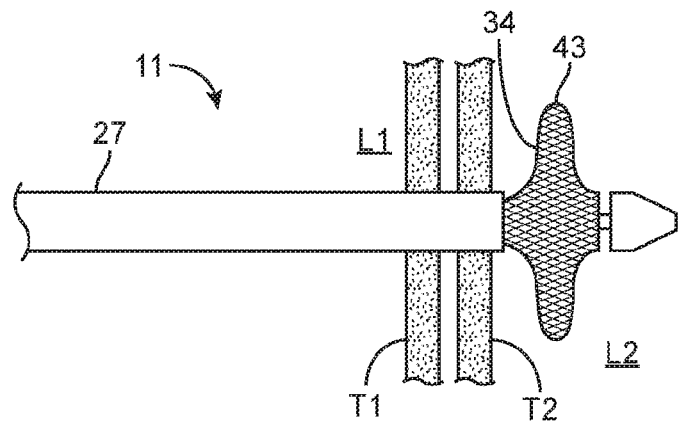
FIGS. 4A-4C illustrate a process for deploying a stent in accordance with some embodiments.
Figure 4B:
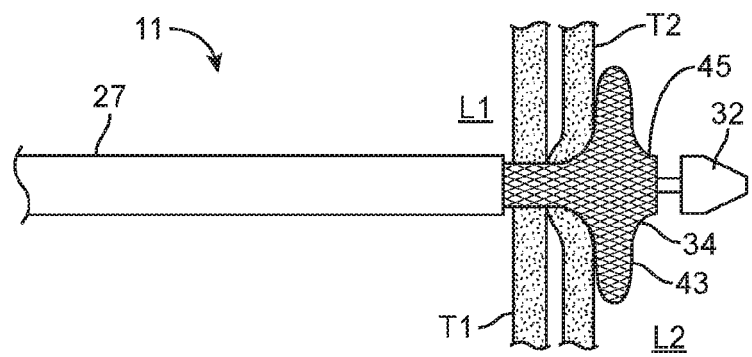
Figure 4C:
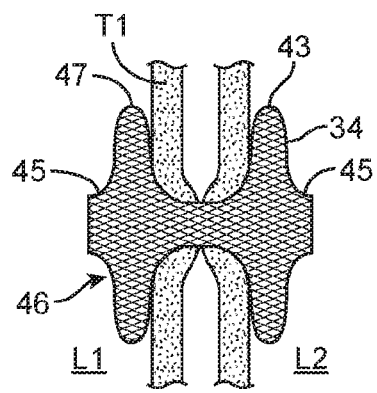

FIGS. 4A-4C illustrates a schematic of a stent delivery to form an anastomosis between two body lumens. Once the catheter 11 has successfully entered second body lumen L2, the distal flange 43 of the stent 34 may be deployed by partially retracting the sheath 27 as illustrated in FIG. 4A. The distal flange 43 may then be drawn proximally against the wall of T2, to establish apposition of the luminal walls during the remainder of the deployment procedure as shown in FIG. 4B. The flange 43 may be deployed by further retracting the sheath. After the tension has been applied using the distal flange 43, the sheath 27 may be further retracted to deploy the proximal end 46 of the stent 34 to fully deploy the stent 34 so that the proximal flange 47 engages a luminal surface of the first tissue layer T1 as shown in FIG. 4C. After the stent is deployed, the catheter including all components may be removed by detaching the handle from the endoscope and withdrawing the entire structure. A central passage or opening through the stent provides for a fluid communication between lumens L1 and L2. The illustrated stent 34 has an optional outer cuff or lip 45 at either end of the stent. The optional cuff or lip 45 can be configured to improve the flow of food and partially digested food. Any of the stents described herein can be deployed using the methods illustrated in FIGS. 4A-4C and FIGS. 20-30.

The stents described herein can also be deployed using general surgery devices such as a laparoscopic delivery device. The devices can be used in any laparoscopic based procedure where an anastomosis is formed. The systems described herein can be used to create a wide range of anastomoses between many types of lumens using a laparoscopic approach.

There are several hundred thousand surgical anastomoses performed each year by physicians; however, there is no method for standardization of this anastomosis. A surgical anastomotic device disclosed would allow physicians to standardize care, prevent prolonged hospital stays due to anastomotic leakage, and re-interventions due to anastomotic strictures. Currently there is no known device for delivery of such therapy through a laparoscopic tool. A laparoscopic based delivery system is disclosed herein that allows the physician to deliver an anastomotic device, such as a stent.

The laparoscopic based delivery system comprises of multiple components allowing for the controlled delivery of either the distal and/or proximal end of the stent as well as the cylindrical "saddle" portion of the stent. The laparoscopic based delivery system can include a handle, shaft, actuating mechanism for deploying the anastomotic device (e.g. stent), and an anastomotic device as shown in the embodiment illustrated in FIGS. 5A-5C. The shaft can be rigid. The actuating mechanism can be configured to selectively deploy a first end and second end of the anastomotic device. The anastomotic device can be held in a compressed position using a sheath, tubing, or other physical restraint to apply radial compression to the anastomotic device. Examples of radial restraints include perforated tubing, heat shrink tubing, biodegradable tubing, wires, hooks, or other removable or adjustable radial restraints. The radial restraint is configured to be removed through the laparoscopic entry port. The delivery device can rotate or move the stent holder relative to the shaft of the delivery device to position the stent relative to the target location as shown in FIG. 5A.

Figure 5A:
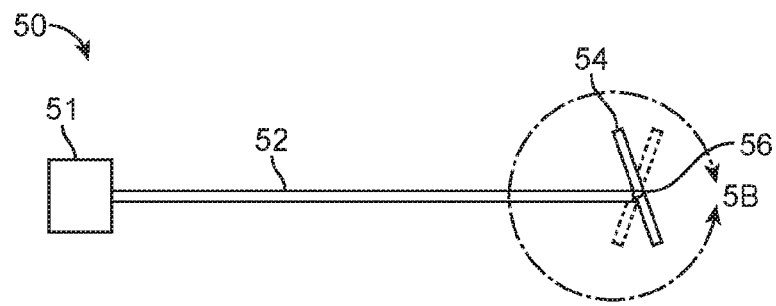
FIGS. 5A-5C illustrate a laparoscopic surgical device for deploying a stent in accordance with some embodiments.
Figure 5B:
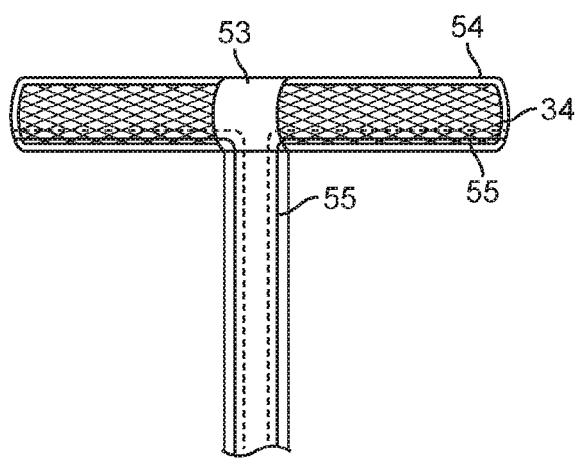
Figure 5C:
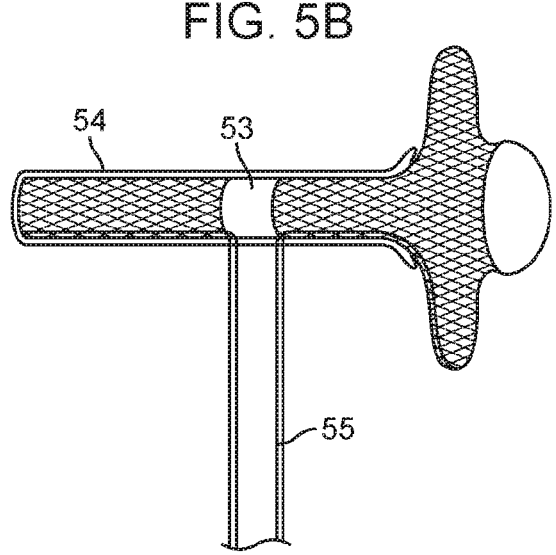
Figure 8A:
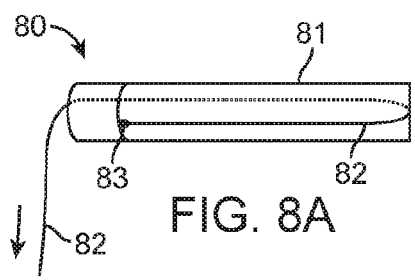
FIGS. 8A-8B illustrate a laparoscopic surgical device in accordance with some embodiments.
Figure 8B:
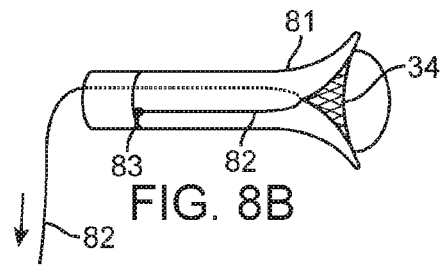

The anastomotic device can be deployed by removing the radial compression and allowing the anastomotic device to expand a shown in FIGS. 5B, 5C, and 8B. The opposing ends of the anastomotic device can be deployed separately and sequentially.

An actuating mechanism can be used to remove the radial compression from the stent. Examples of actuating mechanisms include a moveable sheath, wire, hook, or other structure for converting axial movement along the shaft of the laparoscopic delivery device to lateral movement along axial length of the stent. The actuating mechanism can be used to pull back the sheath or remove the structure radially compressing the stent.

FIGS. 5A-5C illustrate a laparoscopic surgical device 50 for deploying a stent 34 in accordance with some embodiments. The laparoscopic device 50 includes a handle 51, shaft 52, and stent holder 54. The shaft 52 can grasp the stent 35 with a removable clamp 53. The device 50 can include an articulation point 56 to change the orientation of the stent 34 and stent holder 54 relative to the axis of the shaft 51. Additional details of the stent holder 54 and stent actuation mechanism are illustrated in FIG. 5B. The stent holder 54 includes a heat shrink or other removable tubing. Each end of the stent 34 is held in radial compression by heat shrink tubing. The heat shrink tubing can be connected to an actuating mechanism such as the pull-wires 55 shown in FIG. 5B. The pull-wires 55 can be pulled to remove or tear the perforated heat shrink tubing 54, which deploys an end of the stent 34 as shown in FIG. 5C. Each wire can be connected to either a distal end or proximal end of the radial restraint of the stent 34. The wires can independently deploy the distal or proximal ends of the stent or they may be used to actuate both segments at the same time.

Figure 6:
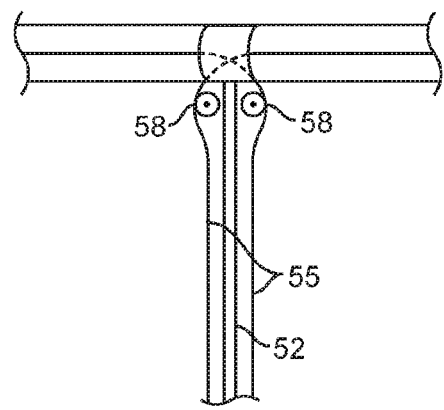
FIG. 6 illustrates a laparoscopic surgical device in accordance with some embodiments.

Removing the radial restraint of the stent can be accomplished using different structures. FIG. 6 illustrates a laparoscopic surgical device in accordance with some embodiments. FIG. 6 illustrates a portion of a delivery device that uses a wheel or pulley 58 adjacent to the delivery shaft 52 near where the shaft connects with the stent holder. The wheels can translate axial movement along the delivery shaft 52 to axial movement along the axis of the stent holder 54. The pull-wire 55 can be pulled from the device handle 51 with the movement translated to movement along the axis of the stent 34 to cut and remove the radial restraint. The pull-wires 55 can be inside or outside of the radial restraint.

Figure 7A:
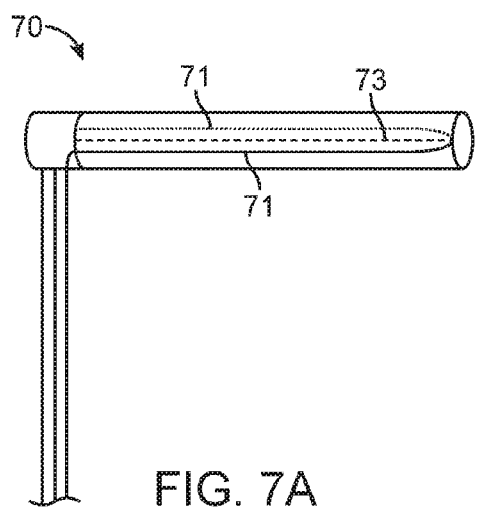
FIGS. 7A-7B illustrate laparoscopic surgical device in accordance with some embodiments.
Figure 7B:
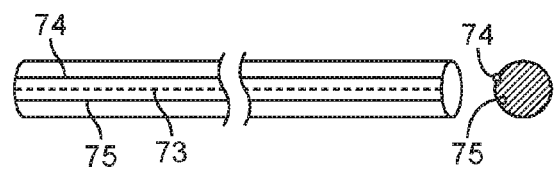

FIGS. 7A-7B illustrate laparoscopic surgical device 70 in accordance with some embodiments. FIG. 7A illustrates additional arrangements between the radial restraint and pull-wires or cords 71. The pull-wire 71 can contact the radial restraint along an interior wall and be doubled back along an outside of the wall of the radial restraint. Pulling the wire or cord cuts the radial restraint thereby allowing the stent to expand. The radial restraint can optionally include a perforation 73 to facilitate the tearing of the restrain along the perforation 73. FIG. 7B illustrates another example of the cord/wire arrangement. One or more wires 74, 75 could be embedded longitudinally on either side of a perforation 73 in the radial restraint.

FIG. 8A-8B illustrates another example of the use of a pull-wire 82 to deploy an end of a stent 34 from a laparoscopic device 80 in accordance with some embodiments. The illustrated radial restraint 81 is a perforated heat shrink material. The pull wire 82 is illustrated as under the heat shrink material 81 and on the exterior of the heat shrink material 81. The pull wire can be pulled towards the center of the stent to separate the heat shrink material and deploy the end of the stent as shown in FIG. 8B. The pull-wire 82 can be secured or attached to the clamp of the device 80 at connection point 83.

Figure 9A:
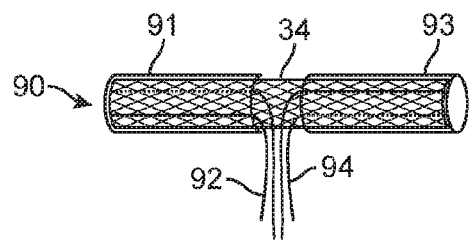
FIGS. 9A-9E illustrate a laparoscopic surgical device in accordance with some embodiments.
Figure 9B:
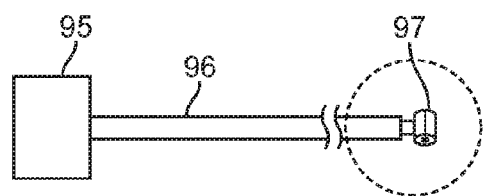
Figure 9C:
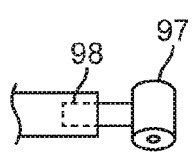
Figure 9D:
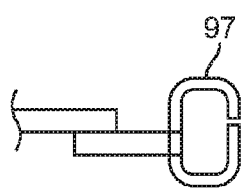
Figure 9E:
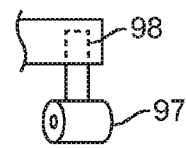

FIGS. 9A-9E illustrate a laparoscopic surgical device and a stent cartridge for use with the laparoscopic surgical device in accordance with some embodiments. A stent cartridge 90 is illustrated in FIG. 9A and includes a stent 34, a first portion of shrink tube 91 holding a first end of the stent, a second portion of shrink tube 93 holding a second end of the stent, a first pull-wire 92 running along the first portion of the shrink tube 91 and stent for deploying the first end of the stent, and a second pull-wire 94 running along the second portion of the shrink tube 93 and stent for deploying the second end of the stent. The removable cartridge 90 can be held in place using a clamp or other releasable securing mechanism. FIGS. 9B-9E illustrate a laparoscopic device handle 95 and shaft 96 with a clamp 97 that can removably engage with the stent cartridge 90. The laparoscopic device handle 95, shaft 96, and camp 97 are reusable. The stent cartridge 90 can be replaced for each surgical procedure. The laparoscopic handle includes the clamp 97 for holding the stent cartridge 90 includes an articulation point 98 to rotate the stent cartridge orientation. FIG. 9D illustrates the clamp 97 with two movable semi-circular pieces that can open and close to engage with the stent cartridge 90. This delivery system also allows for the independent actuation of both distal and proximal sections of a shrink tube 91, 93 covering the distal and proximal section of the stent 34. The articulation point 98 allows the physician an additional degree of movement within the patient if needed during positioning or deployment of the stent 34. In this embodiment either the distal segment or the proximal segment can be deployed independently as per physician preference by pulling either of the pull-wires 92 or 94.

Figure 10:
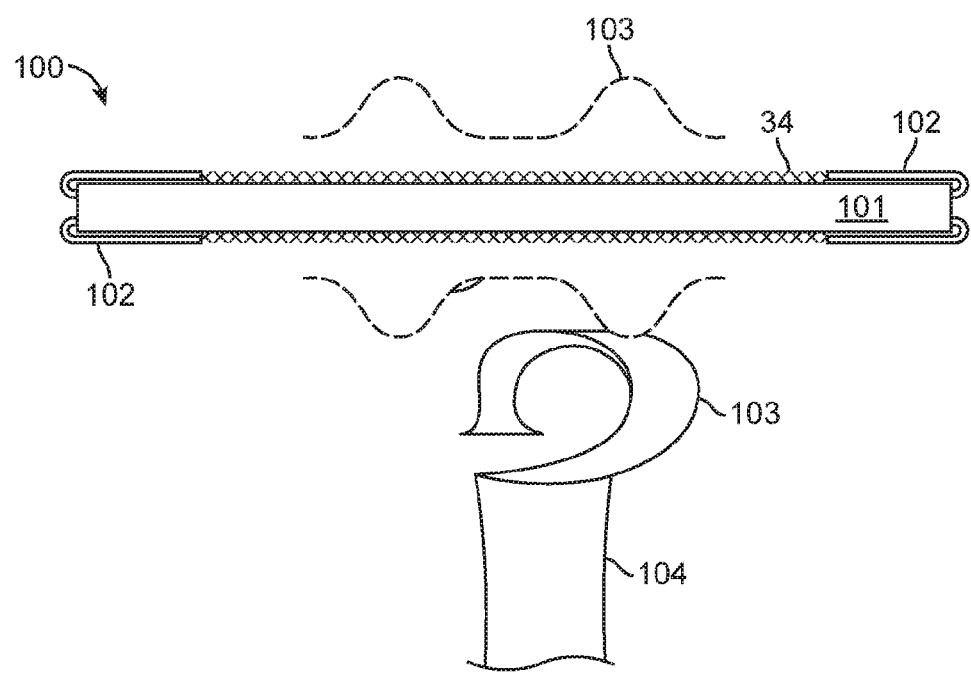
FIG. 10 illustrates a laparoscopic surgical device in accordance with some embodiments.

FIG. 10 illustrates a laparoscopic surgical device in accordance with some embodiments. The stent cartridge 100 can be used with the laparoscopic systems disclosed herein. FIG. 10 also illustrates another embodiment of a radial restraint for the stent. The stent 34 can be radially restrained to a tube 101 with a tensile force applied using wires, strings, or hooks 102 to secure the ends of the stent 34 against the tube 101. The radial restraint can be removed to deploy the stent ends such that the stent can expand to an expanded configuration 103. The device illustrated in FIG. 10 can be used with a laparoscopic type device. The device can access the target organs through the peritoneal cavity and secure the stent cartridge 100 using clamp 103 and shaft 104. The clamp 103 can be used to remove the wires, strings, or hooks 102 to deploy the stent. The clamp 103 includes a release mechanism to release the grip on the stent after deployment of the stent. After deployment of the stent, the tube 101 and stent 34 are released from the delivery device. The 101 tube is within the volume of the stent 34. The tube 101 can then be removed endoscopically. When the stent is deployed between the fundal pouch and intestines the tube 101 can be retrieved through either the fundal pouch or intestines. The tube 101 can be malleable to facilitate movement through tight passageways but rigid enough to hold the stent in place. In some embodiments the tube 101 can be biodegradable.

Figure 11A:
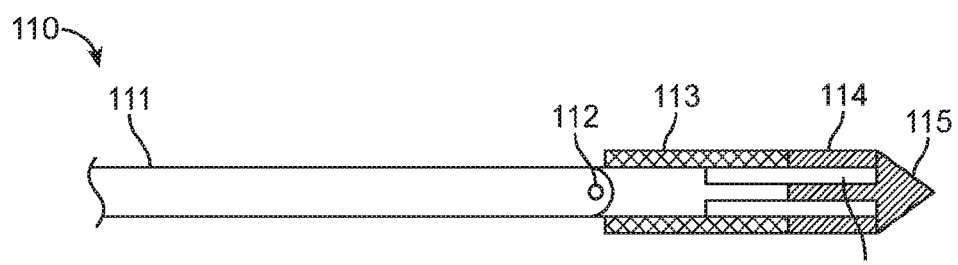
FIGS. 11A-11D illustrate a laparoscopic surgical device in accordance with some embodiments.
Figure 11B:
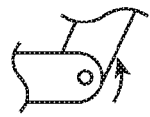
Figure 11C:
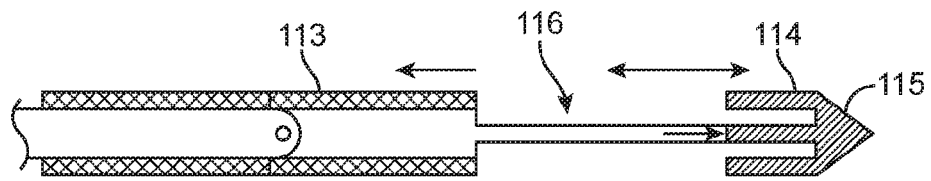

Another embodiment of a laparoscopic tool 110 for deploying a stent is illustrated in FIGS. 11A-11C. The stent can be incorporated into a stent compartment 116 at an end of the laparoscopic device 110 as illustrated in FIGS. 11A-11C. The device 110 includes an articulation point 112 to change the orientation of the stent compartment relative to the shaft 111 of the device 110. The delivery device includes a nose cone 115. The nose cone 115 can be used for entry into the body. The nose cone 115 can be movable relative to the delivery shaft 111. The device 110 includes two sheath portions 113, 114 configured to hold the stent in a restrained position. A proximal portion 113 or section can cover a proximal portion of the stent. A separate distal portion 114 of the sheath can restrain a distal portion of the stent. The proximal portion of the sheath 113 and distal portion of the sheath 114 are moveable relative to each other. The device 110 can separately move the proximal 113 and distal 114 portions of the restraint/sheath to deploy the stent as shown in FIG. 11C. The distal portion of the sheath 114 can move distally to allow the distal portion of the stent to expand. Similarly the proximal portion of the sheath 113 can move proximally to allow the proximal portion of the stent to expand. The device 110 can be introduced to the peritoneal cavity laparoscopically and then penetrate a body lumen, such as a portion of the intestines. The device 110 can then travel through the body lumen to the target location (optionally penetrating additional body lumens) followed by deployment of the stent.

Deploying the sheath can be accomplished in a variety of ways. In some embodiments the nose cone can hold the sheath and stent in place and move distally/forward thereby pulling the proximal portion of the stent away from the proximal restraint. In some embodiments the proximal portion of the stent can also be deployed using a push rod type arrangement where the proximal end of the stent is pushed distally to deploy the proximal flange. In some embodiments the nose cone can also be pushed distally while holding the stent in place to remove the distal sheath, thereby deploying the distal end of the sheath. In some embodiments an inflatable structure can also be used to selectively hold the stent or sheath in place. In one embodiment the distal segment deploys with a pushrod type actuation mechanism to move the nose cone and sheath while the proximal segment deploys with a pull type mechanism to pull the sheath proximally to deploy the proximal stent flange. In one embodiment the stent can be wrapped with a removable material to hold the stent in the radially constrained position. The stent can be deployed by removing the wrapper. In one embodiment the stent can be tied in a radially constrained position. The ties can be removed to deploy the stent to an expanded configuration.

Figure 11D:
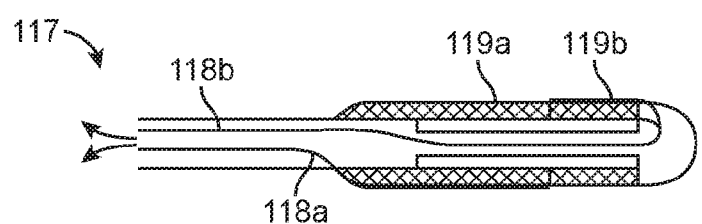

FIG. 11D illustrates another embodiment of a delivery device 117 including pull-wires 118a, 118b each configured to remove a portion of a radial restraint 119a, 119b. The radial restraint can be a sheath or removable tubing. The sheath can include one or more pieces. A proximal portion of the sheath 119a can cover a proximal portion of the stent. The proximal portion of the stent can be deployed using a proximal pull-wire 118a to move or remove the proximal sheath 119a restraining the proximal portion of the sheath. A separate distal portion of the sheath 119b can restrain a distal portion of the stent. The distal sheath 119b can be separately moved or removed using a distal pull wire 118b.

In some embodiments the delivery system includes a laparoscopic tool with a handle, shaft, and replaceable cartridge. The replaceable cartridge can include the distal tip of the delivery system and a preloaded anastomotic device. The physician can operate the system within the patient to deploy the anastomotic device in the target location. The handle and shaft can be sterilized after the surgical procedure and used in a subsequent surgical procedure with a new cartridge having the anastomotic device, such as the stent cartridges described in FIGS. 5A-5C, 10, 12A-12F, and 13A-13C.

Figure 12A:
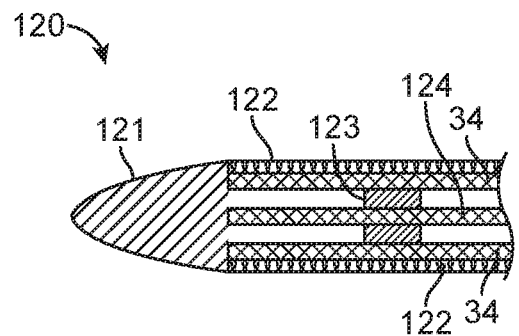
FIGS. 12A-12F illustrate various aspects of embodiments of a stent cartridge device in accordance with some embodiments.
Figure 12B:
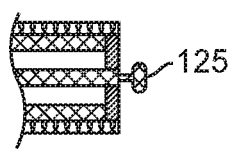
Figure 12C:
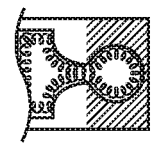
Figure 12D:
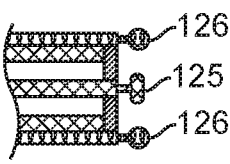
Figure 12E:
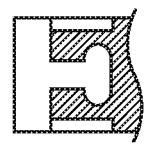
Figure 12F:

Additional examples of stent cartridges and engagement structures are illustrated in FIGS. 12A-12F and 13A-13C. The engagement structures can be used to removably attach a reusable delivery device including a handle and shaft portion. FIGS. 12A-12F illustrate a portion of a delivery device including a stent cartridge with various mating structures. The end of the stent cartridge can use a mechanical means to mate with a laparoscopic handle based delivery system. A cartridge 120 containing a stent 34 is illustrated in FIG. 12A. The cartridge 120 can include a rigid inner member 124, a nose cone 121, an inner pocket for housing the stent 34, a sheath 122 with mating structures 126, a stent engagement ring 123, and an inner mating structure 125 for engaging rigid inner member with the rigid laparoscopic handle. The separate mating structures can be independent controlled by the laparoscopic handle. The sheath mating portion can separately control the outer sheath to move the sheath independently relative to the interior portion. The interior mating portion 125 can control the movement of the inner shaft 124 and nose cone 121. The laparoscopic handle can be actuated to draw back the sheath 122 and release the stent 34. FIG. 12A illustrates a cartridge 120 with a stent 34 held in place by the outer sheath 122 and a stent retention device 123 coupled about the inner deployment shaft 124. Various mating structures are also illustrated in FIGS. 12B-12F. FIG. 12B-C illustrates two different cross-sectional views of the end of the cartridge 120 including the interior mating portion 125. FIGS. 12D-E illustrate two different cross-section views of another embodiment of the end of a cartridge 120 with an interior mating portion 125 and a sheath engagement portion 126. FIG. 12F illustrates another embodiment of a mating structure.

FIG. 13A illustrates a cartridge device 130 with mating structures 133, 134 for the outer sheath 131 and inner deployment shaft 136, respectively. FIG. 13A illustrates the nose cone 132 pushed distally to reveal a portion of the stent compartment 134. FIG. 13B is an enlarged portion of the outer sheath mating structure 133 and inner deployment shaft mating structure 134. FIG. 13C illustrates an enlarged portion of the nose cone 132, sheath 131, inner deployment shaft 136, and stent compartment 135.

Figure 14:
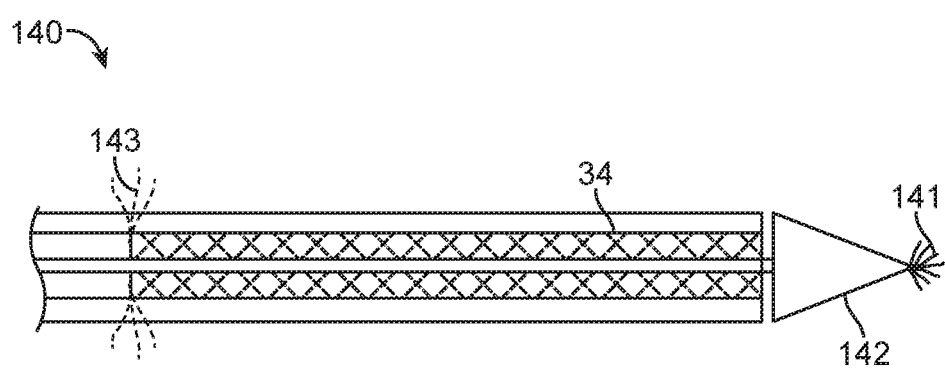
FIG. 14 illustrate a portion of a device with a fiber optic lighting system in accordance with some embodiments.

The delivery devices disclosed herein can include a means for visualization of the device and stent. Examples of visualization include ultrasound, fluoroscopy, direct visualization and other methods. Direct visualization can be facilitated by the use of a light, such as a fiber optic assembly. FIG. 14 illustrates a distal portion of a delivery device 140 with fiber optic lights 141, 143. Fiber optic lights can assist the surgeon with visualization in laparoscopic surgical procedures. The fiber optic lights can help identify the position of the device in body lumens such as the stomach, colon, or intestines. The device can include multiple fiber optic lights as illustrated in FIG. 14. The device illustrated in FIG. 14 includes fiber optic lights 141 at the tip of the device adjacent to the nose cone 142. FIG. 14 also illustrates fiber optic lights 143 along the shaft of the delivery device adjacent to a proximal side of the stent 34/stent compartment. The fiber optic light source can also be adjacent to the ends of the stent compartment to assist the surgeon in identifying the stent position during the surgical procedure. Different colored lights can be used to identify different locations on the device. The nose cone and other portions of the delivery device can be transparent. Fiber optic light sources could be located adjacent to the transparent portions such that the light is visible through the transparent portions. For example, the fiber optic lights source could be located inside a transparent nose cone and/or inside a transparent portion of the delivery shaft.

Fluoroscopy can also be used for visualization of the devices disclosed herein. An intraluminal connection port can be incorporated into the devices disclosed herein to allow for introduction of a fluid diagnostic via the delivery system. For example a Toue-Borst connector can be used. A fluorescent die can be introduced via the intralumenal connection port for fluoroscopy.

The devices disclosed herein can be used to form one or more anastomoses. For example, a catheter based stent delivery device can be used with an endoscope to form one anastomosis, for example between to portions of the intestines. An endoscopic based device could be used to form an anastomosis between the fundal pouch and a portion of the intestines, such as the jejunum. A combination of a laparoscopic based device and a catheter device as described herein could also be used to form a single anastomosis. For example, the catheter based device could deploy a first half of a stent and a laparoscopic based device could deploy the second half of the stent. The stent halves could then be joined to form the anastomosis as shown in FIGS. 19A-19D.

The tip designs disclosed herein can be designed to minimize or prevent leakage from the opening cut in the passage of the targeted anatomical structures given the diameter of the device entering the anatomical structures. In some embodiments the delivery device has a tip with a conical shape. In some embodiments the delivery device has a tip with a shape other than a conical shape. In some embodiments the delivery device has a tip that can be blunt, round, or pointed. In some embodiments the delivery device has a tip with a cautery mechanism, such as an energized tip. Energy can be supplied to the tip of the device, such as radiofrequency (RF), high-frequency (HF), or other types of energy. The energized tip of the device can then cut through the tissue to create luminal access into the target anatomical structure. In some embodiments the delivery device has a balloon or expansion member to allow for dilation of the stent or tissue passage.

In some embodiments the delivery device has a balloon or expansion member to allow for dilation of the stent or tissue passage before or after deployment of the stent. For example, a self-expanding stent can be deployed followed by a post-deployment dilation using a balloon to encourage the self-expanding to achieve the expanded configuration faster than the time required for the stent to self expand. In some embodiments the devices disclosed herein can include an energized tip.

In some embodiments disclosed herein a guidewire is used for guidance into the target anatomical structure. When a guidewire is used the device can include a guidewire lumen and hole in the tip for the wire to exit distally. The devices disclosed herein can follow a guidewire placed within the target anatomical structure. The guidewire can be placed in the target anatomical structure using a needle, such as a 19 gauge needle. The devices can follow the guidewire until the tip is at the target anatomical structure.

In some embodiments the devices can be used without a guidewire.

In some embodiments the devices disclosed herein can be flexible to facilitate passageway through body lumens. For example, catheter based devices disclosed herein can be flexible to be used with an endoscope.

In some embodiments the devices disclosed herein can be rigid or include a rigid shaft. For example the laparoscopic based devices can use a rigid shaft for facilitating access into the peritoneal cavity. In some embodiments the laparoscopic devices can include some flexibility.

In some embodiments the devices disclosed herein can be used to deploy a stent to form an anastomosis between any of the stomach, small intestines (duodenum, jejunum, ileum), and large intestines (cecum, colon), rectum, biliary structure, or esophagus.

A stent or tissue anchor can be used to form the anastomosis in the GI tract. The stent can reduce the leakage rates of the anastomosis as compared to the original surgical anastomosis alone and also allow for fluid, partially digested food, and food passage through the stent. Stents can save time and prevent leakage over stapling and other surgical anastomosis methods. Stents are also applicable to colon resection processes with the stent being used to make the anastomosis between the cut ends of the intestines. The stents disclosed herein can also be used with basic endoscopic tools, catheters, laparoscopes, and general surgery tools. Examples of methods and devices for deploying the stents are discussed herein.

Examples of tissue stents and anchors are discussed in greater detail below. Examples of stents and tissue anchors that can be deployed using the devices and methods disclosed herein are disclosed in co-owned U.S. Patent Publication No. 2009/0281557 and U.S. Patent Publication No. 2013/0310833. Devices and methods for placing stents are also disclosed in co-owned U.S. Pat. No. 8,357,193 and U.S. Patent Publication No. 2013/0310833. Additional devices and methods for placing stents and anchors are disclosed in U.S. Provisional Application No. 61/648,544 filed on May 17, 2012 and U.S. Provisional Application No. 61/727,629 filed on Nov. 16, 2012. The devices and methods disclosed in these applications can be used with the concepts disclosed herein.

The stents disclosed herein can be configured to promote the flow of fluid, partially or fully digested food, and food through the internal pathway of the stent. The flanges of the stent can be configured to decrease the possibility of food becoming lodged within the stent. The ends of the flanges can also be configured to reduce the likelihood of trapping food or partially digested food and to better receive and dispense food, such as by angling the ends away from the interior volume of the stent or curling the ends outward away from the interior volume of the stent. In one embodiment the stent ends can be configured to promote the flow of material in one direction.

Other design considerations for the stents described herein include the manufacturability of the stents and the ability to load and deploy the stent using the devices disclosed herein.

The stent designs also offer improved lateral strength and pullout force over conventional stents. The pullout force can be determined using two different tests, a stent pull-out force test and an implant anchor pull-pout test.

For the pull-out force test the stent is tested in a fully expanded configuration. The stent is deployed through a hole in a material sized to accommodate the expanded diameter of the cylindrical saddle region of the stent. The hole in the material can be around 10 mm or 15 mm depending on the stent size. The stent pull-out test measures the force required to deform the distal flange of the fully expanded stent and to pull the expanded distal flange of the stent through the opening. In some embodiments the stent pull-out force is greater than about 260 grams (about 2.55 N). In some embodiments the stent pull-out force is greater than about 300 grams (about 2.94 N). In some embodiments the stent pull-out force is greater than about 400 grams (about 3.92 N). In some embodiments the stent pull-out force is greater than about 500 grams (about 4.9 N). In some embodiments the stent pull-out force is greater than about 550 grams (about 5.39 N). In some embodiments the stent pull-out force is greater than about 600 grams (about 5.88 N). In some embodiments the stent pull-out force is greater than about 700 grams (about 6.86 N). In some embodiments the stent pull-out force is greater than about 800 grams (about 7.84 N). In some embodiments the stent pull-out force is greater than about 900 grams (about 8.82 N). In some embodiments the stent pull-out force is greater than about 1000 grams (about 9.8 N).

For the implant anchor test the strength of the distal flange is tested while the proximal flange of the stent is held by the catheter device in a constrained position. The distal flange is deployed on the other side of a rigid material having a hole sized to accommodate the shaft of the catheter. The catheter can be pulled with the force measured that is required to deform the distal flange and pull the distal flange through the hole in the rigid material. In some embodiments the stent has an implant anchor test strength of greater than about 1 N. In some embodiments the stent has an implant anchor test strength of greater than about 2 N. In some embodiments the stent has an implant anchor test strength of greater than about 3 N. In some embodiments the stent has an implant anchor test strength of greater than about 4 N. In some embodiments the stent has an implant anchor test strength of greater than about 5 N. In some embodiments the stent has an implant anchor test strength of greater than about 6 N. In some embodiments the stent has an implant anchor test strength of greater than about 7 N. In some embodiments the stent has an implant anchor test strength of greater than about 8 N. In some embodiments the stent has an implant anchor test strength of greater than about 9 N. In some embodiments the stent has an implant anchor test strength of greater than about 10 N. In some embodiments the stent has an implant anchor test strength of greater than about 15 N.

The stents disclosed herein also provide benefits over conventional rigid rivet type anastomotic devices used in the GI tract because the stents firmly and atraumatically engage the tissue walls and do not form necrotic tissue. The reduced formation of necrotic tissue promotes faster formation of a healthy anastomosis. The stents disclosed herein are also configured to be retrievable and removable after formation of the anastomosis.

A variety of examples of stent configurations and shapes are illustrated in FIGS. 15A-15G, 16A-16J, 17A-17C, and 18A-18D that can be used with the devices disclosed herein. The tissue anchor or stent can be made out of a shape memory alloy such as Nitinol. The stents can be self-expanding such that the stent expands from a constrained tubular position to the expanded configurations illustrated in FIGS. 15A-15G, 16A-16J, 17A-17C, and 18A-18D.

The stents disclosed herein can include a covering or membrane over the entire exterior of the tissue anchor, for example a silicon covering. The covering or membrane inhibits tissue ingrowth and minimizes fluid leakage when the stent is implanted. Reducing tissue ingrowth improves the removability of the stents after formation of the anastomosis. In contrast to vascular stents, which are typically not designed to be moved or retrieved, the stents illustrated herein are collapsible and designed to be removable and retrievable. The stents also do not include barbs or other sharp projections typically used in vascular stents to permanently secure the stent to the blood vessel.

The stent shapes can vary. For example the end or flange shape can be optimized to improve the strength of the stent and to provide a sufficient amount of linear force opposing each tissue plane while allowing smooth food flow through the inner opening of the composite structure. End shapes can be described as "bell-like", consisting of multiple structural folds, having a plurality of inflection points, etc. The inflection point can be considered a point of a curve at which a change in the direction of curvature occurs. Additional ends might be rolled or may protrude retrograde against the tissue plane. Alternate designs might consist of a mouth that is wider than the inner diameter of the device.

FIG. 15A illustrates a cross section of an embodiment of a stent 150 with a cylindrical saddle region 151, flange 152 with an end 153 configured to bend back towards flange 154, flange 154 with an end 155 configured to bend back towards flange 152. The flanges 152, 154 and ends 153, 155 are configured to hold the tissue walls T1, T2 in apposition. The distal portion of the flanges 152, 154 are curved to reduce trauma to the tissue walls. FIGS. 15B and 15C have a similar configuration to FIG. 15A but with the ends 153, 155 of the stent further curled. FIG. 15B shows the ends 153, 155 curled in roughly a half circle and FIG. 15C has ends 153, 155 forming approximately a full circle. The ends 153, 155 of the stents in FIGS. 15B-C can atraumatically engage the tissue with increased strength from the additional curling on the distal ends of the stent structure.

FIGS. 15D-15G illustrate additional cross-sectional views of stent structures. FIG. 15D illustrates a stent 150 with flange structures 152, 154 projecting away from the cylindrical saddle region 151. The cylindrical saddle region 151 has a diameter of D1 and the outer flange structure 152, 154 has a larger diameter D2. FIG. 15E illustrates a stent 150 with flange structures 152, 154 curling outward and away from the interior volume of the cylindrical saddle region 151. FIG. 15F illustrates flange structures 152, 154 that project away from the cylindrical saddle region 151 and have curled ends 153, 155. The curled end can provide additional lateral strength to the stent. FIG. 15G illustrates flange structures 152, 154 that project away from the interior volume of the cylindrical saddle region 151 and further include double walled flange structures to increase the strength of the stent 150 and to further engage atraumatically with the tissue walls when implanted.

FIGS. 16A-16J illustrate a variety of partial cross-sections for stent flange configurations. Some flange structures can have a volume within each flange that might trap food or other material passing through the stent. The flange can be designed to minimize the chance of food or other material getting trapped within the internal volume of the stent or stent flange. The stents illustrated in FIGS. 16A-16I have flange structures that are designed to minimize food and partially digested food getting trapped or stuck within the flange volumes.

FIG. 16A illustrates a partial cross section of a stent 160 with a flange structure 162 having a plurality of inflection points. The inflection points create radial bends in the three-dimensional stent structure. The flange 162 wall projects away from the cylindrical saddle region 161 (a first inflection point) then bending back towards the center of the longitudinal pathway 164 of the stent 160 (two more inflection points) followed by bending back again away from the center of the longitudinal pathway 164 of the stent 160 (two more inflection points) and an additional bend at the stent end 163 (one more inflection point). Each of the bends can be considered an inflection point. The stent 160 illustrated in FIG. 16A has 6 inflection points. The inflection points can add additional strength to the stent flange. The stent has an open end with a diameter that is greater than the diameter of the cylindrical saddle region 161 to reduce the likelihood of food getting stuck in the stent and to promote the flow of food and partially digested food through the stent body. The additional inflection point can increase the lateral strength and pullout force of the expanded stent.

FIG. 16B illustrates a stent 160 with a flange structure 162 having seven inflection points. The structure is similar to the stent illustrated in FIG. 16A but the outer stent wall angles back towards the center of the longitudinal pathway 164 at the end 163.

FIG. 16C illustrates a stent 160 with a flange structure 162 including a curled stent end 163. The curled end curls back towards the cylindrical saddle region 161 forming a circular cross-section. The end 163 of the stent flange bends back towards itself so that the fluid flow does not flow directly at the end of the stent. This stent configuration further decreases the likelihood food getting stuck within the internal volume of the flange 162.

FIG. 16D illustrates a stent 160 with a flange 162 projecting away from the longitudinal pathway 164 of the saddle region 161 and with an end 163 curling outwards past the outer point of the flange 162.

FIG. 16E illustrates a stent 160 with a flange 162 having five inflection points. The flange 162 projects outward away from the center of the saddle region 161 and then bends back towards the center pathway 164 followed by bending again with the end 163 projecting away from the longitudinal center 164 of the cylindrical saddle region 161.

FIG. 16F illustrates a stent 160 with a flange 162 projecting away from the cylindrical saddle region 161 and forming a curled circular cross-section with the end 163 curled back towards the flange 162.

FIG. 16G is similar to FIG. 16F but with the circular end 163 curling to form greater than a full circle at the end 163 of the stent.

FIG. 16H illustrates a stent flange 162 having multiple bends resembling right angles along with a curled end 163 curling away from the cylindrical center region 161. The right angles can increase the lateral strength and pullout force of the stent.

FIG. 16I illustrates a flange having a sinusoidal outer shape with a curled end curling away from the cylindrical saddle region. The wavy sinusoidal outer shape can increase the lateral strength and pullout force of the stent.

FIG. 16J illustrates a stent cross section one a flange having the structure illustrated in FIG. 16A and a flange illustrates in FIG. 16I. The flange illustrated in FIG. 16A has a wider opened and can be deployed such that it faces the direction of fluid flow. The flange illustrated in FIG. 16I has a narrower outer end and can be used as the opposing end where the material exits the internal volume of the stent.

Figure 17A:
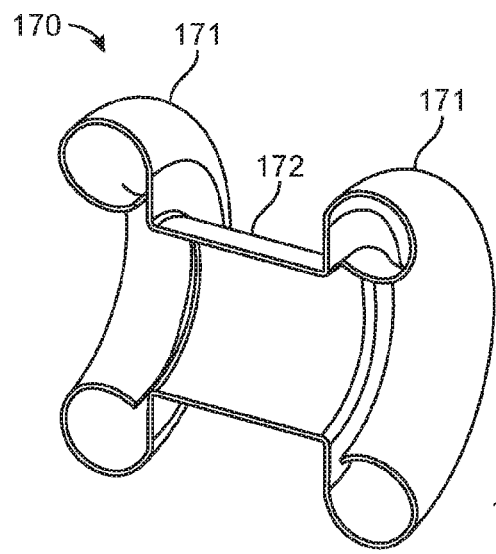
FIGS. 17A-17C illustrate stents in accordance with some embodiments.
Figure 17B:
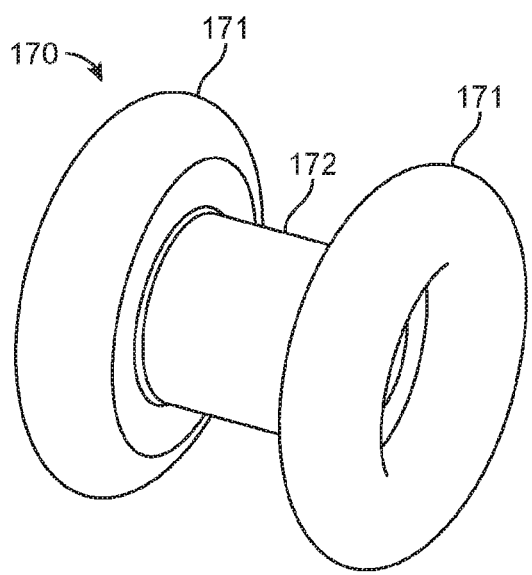
Figure 17C:
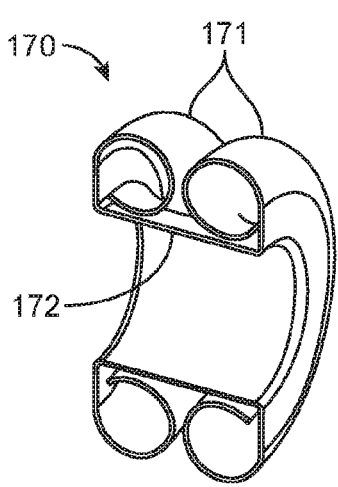

FIGS. 17A-17B are cross-sectional and exterior views, respectively, of a stent 170 in accordance with some embodiments. The flange structures 171 initially project outward away from the stent body and then curl back towards the internal volume of the cylindrical saddle region 172 to form a semi circular flange configuration. The flange provides additional lateral strength and improved pullout force while minimizing the chance of food or partially digested food from getting stuck within the internal volume of the flange. FIG. 17C is an alternate configuration with the semi-circular flange structure 171 curled back towards the cylindrical saddle region 172.

Figure 18A:
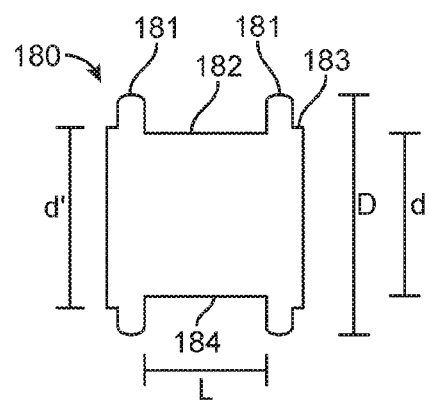
FIG. 18A-18D illustrate cross sections of stents in accordance with some embodiments.
Figure 18B:
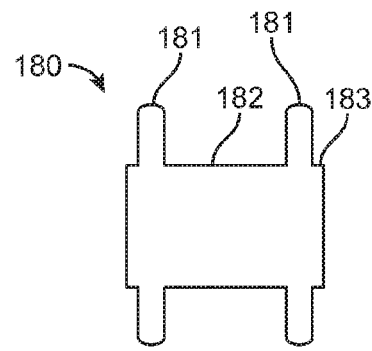
Figure 18C:
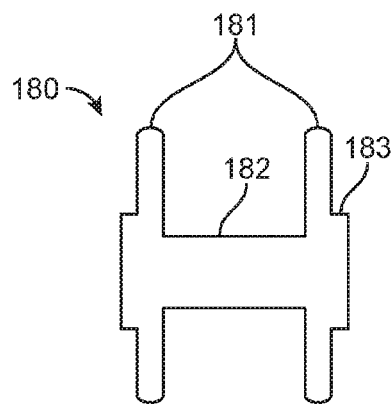

The stent structures shown in FIGS. 18A-18D can be referred to as double-walled flange structures. FIG. 18A illustrates a stent 180 with cylindrical saddle region 182 and a flange 181 with a relatively large open cylindrical region and a wide cuff or lip 183 on the flange structure 181. FIG. 18B illustrates a stent 180 with a smaller internal diameter than FIG. 18A but with a larger double-walled flange 181 for atraumatically engaging the tissue. FIG. 18C illustrates a stent 180 with an outer cuff or lip 183 diameter that is greater than the diameter of the internal cylindrical saddle region.

Figure 18D:
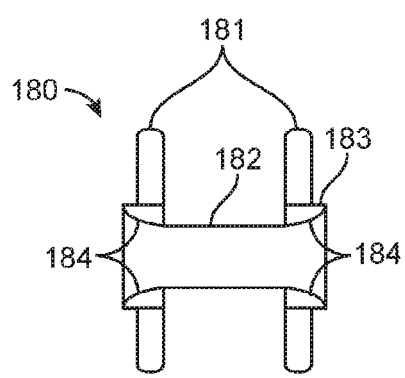

FIG. 18D illustrates an embodiment of a stent 180 similar to FIG. 18C but with a separate plug 184 in the flange 181 to prevent food from getting stuck in the flange volume. The plug can made of a material that is suitable to flow or pass through the digestive track after the stent is removed. In some embodiments the flange can be made out of a biodegradable or bioabsorbable material. The flange plug structure can be used with any of the stent structures disclosed herein.

In some embodiments the stent ends are symmetrical. In some embodiments the stent ends can have different end shapes. The stent end shapes can be selected based on the body lumens and location of the anastomosis and desired physical properties. The stents can be designed to facilitate unidirectional flow as the food or partially digested food should primarily flow in one direction. The unidirectional flow can also exert or require additional strength for the leading stent flange (e.g. proximal flange) that first contacts the flow of material. The proximal flange can be designed with a cross-section that has a stronger pull-out force than the distal flange. The diameter of the opening in the proximal flange can have a wider design than the distal flange to minimize the chances of material getting stuck within the flange. The ends of the proximal flange can also be designed to further decrease the chances of getting food or material stuck in the flange. For example a stent could have the cross-section illustrated in FIG. 16A for the proximal flange with its wider flange end and a flange design like FIG. 16I for the distal flange as illustrated in FIG. 16J.

The dimensions of the stent can be designed to provide a desired hold on the tissue walls along with a desired conduit for fluid flow. For example, the width and diameter of the flange can be optimized to provide the desired properties. A cuff or lip can be provided distally to the flange to provide additional strength. The diameter and length of the cuff can also be optimized to modify the properties of the stent. The diameter of the cuff can be greater than the diameter of the cylindrical hollow portion. This can make subsequent access to the stent easier and decrease the chance of material getting stuck in the flange. The cuff or outer lip can also be shaped to minimize the chance of food or partially digested food getting stuck within the flange volume. For example, the outer cuff or lip can include a wall that projects or curls away from the interior volume of the stent. The diameter and length of the cylindrical portion can be optimized based on the thickness of the tissue walls and desired stent location. The overall length of the stent can also be optimized based on the specific application.

In some embodiments the intralumenal diameter of the saddle region is from about 8 mm to about 40 mm. In some embodiments the intralumenal length of the cylindrical saddle region is from about 15 mm to about 25 mm.

Examples of manufacturing techniques include using laser cutting, weaving, welding, etching, and wire forming. A membrane material such as silicon can be applied to the wire stent frame to prevent the passage of fluid through the stent walls. The membrane material can be applied by painting, brushing, spraying, dipping, or molding.

Figure 19A:
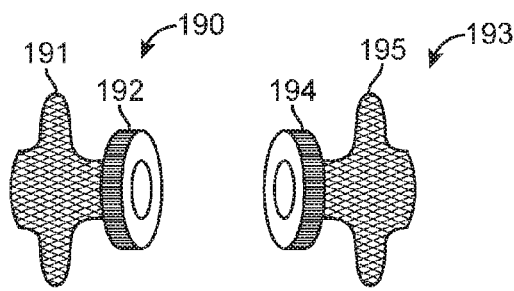
FIG. 19A illustrate a stent with a two-part construction in accordance with some embodiments.
Figure 19B:
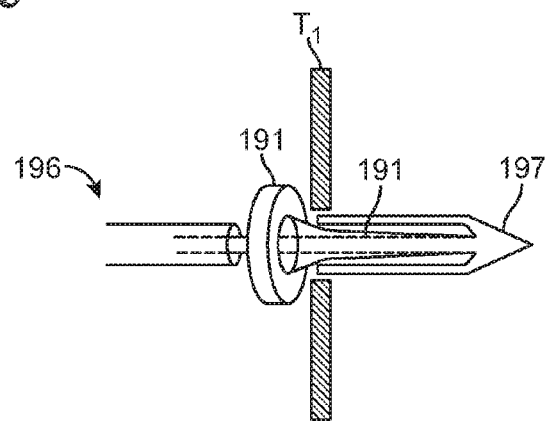
FIGS. 19B-19D illustrate a method for implanting a stent having a two-part construction in accordance with some embodiments.
Figure 19C:
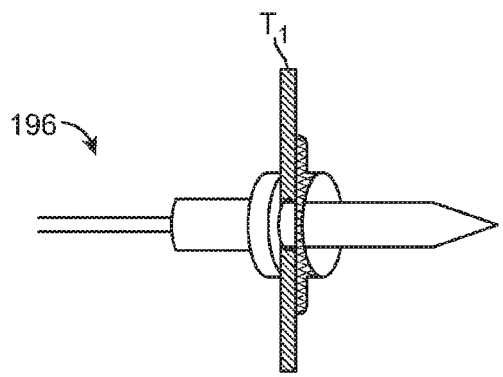
Figure 19D:
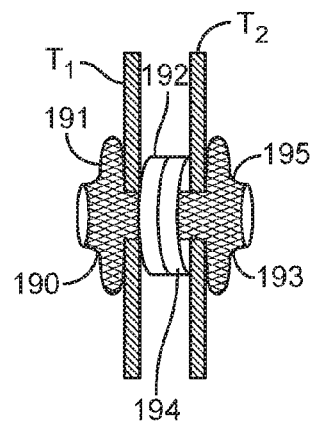

In some embodiments any of the stents disclosed herein can include two half portions. FIG. 19A illustrates two halves of a stent, each with a magnetic ring. FIG. 19A illustrates a first stent half 190 with a flexible flange 191 and magnetic ring 192 and a second stent half 193 with a magnetic ring 194 and flexible flange 195. The magnets can be configured to be attracted to each other. Thus, each half could be separately deployed by a laparoscopic device 196 to the respective target location, e.g. separate sides of the target anastomosis tissues or lumens as shown in FIGS. 19B-19C by deploying the flexible flange 191 by withdrawing a restraint on the flange such as by moving the nose cone 197 forward. The laparoscopic device 196 could be removed through the hollow cylindrical region of the first stent half 190. The magnets 192, 194 could then be joined such that flange 191 engages tissue wall T1 and flange 195 engages tissue wall T2 to form the anastomosis as illustrated in FIG. 19D. Other types of connection are also possible with two half stents. For example, clips, rings, tabs, and other interlocking structures could be used.

Figure 20C:
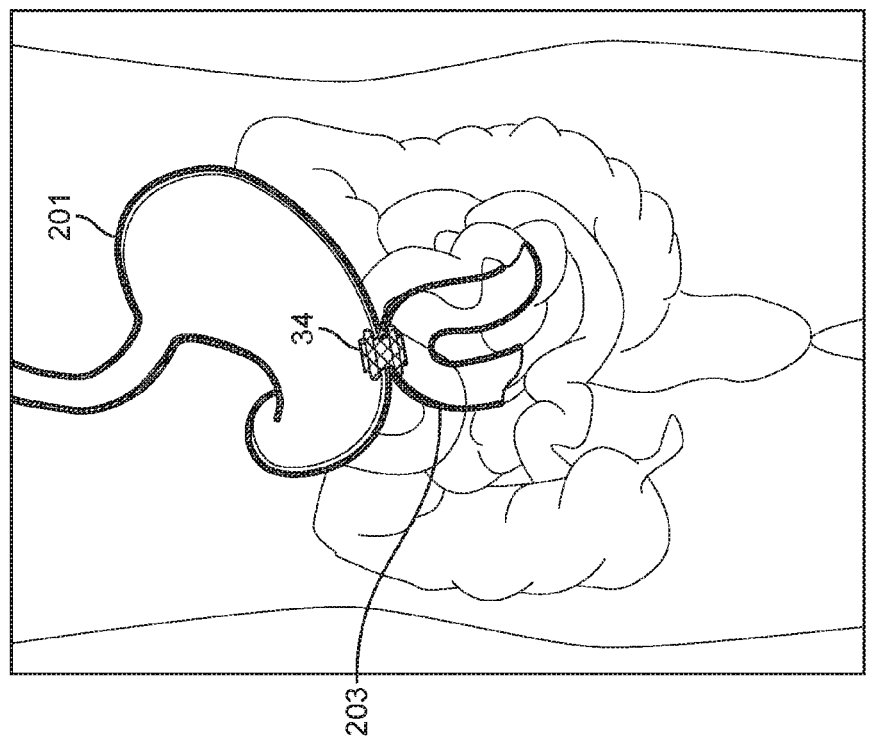

FIGS. 20A-20C illustrate a method for deploying a stent between a stomach and a portion of the intestines in accordance with some embodiments. The procedure illustrated in FIGS. 20A-20C can be referred to as a NOTES procedure. The NOTES procedure is relatively fast and easy but there is increased chance of contamination of the peritoneal cavity because the endoscope and catheter device penetrate the stomach wall and enter the peritoneal cavity in order to locate the target section of the intestines.

An endoscope enters the mouth and is advanced down the esophagus into the stomach. The endoscope can include a plurality of ports. For example, one port can contain a catheter device carrying the stent and a second port can contain a grasper device and/or tools to create an incision. After making an incision in a stomach wall the endoscope 200 can be advanced through the wall of the stomach 201 as shown in FIG. 20A. The endoscope 200 is used to identify the target location in the intestines 203, such as a specific point in the jejunum. The grasper 202 is then used to attach to and gain control of the intestines adjacent to the target location of the intestines 203 as shown in FIG. 20A. A cystotome or other suitable device can be advanced through the second port on the endoscope 200 to obtain guidewire access to the intestines 203. The cystotome can be exchanged over the guidewire for a catheter device 204. The catheter device 204 carrying a stent 34 can follow the guidewire to gain access to the intestines 203. The catheter device 204 can include a dilator such as an energized tip to enlarge the initial penetration into the intestines 203. In some cases the use of a guidewire is optional and the energized tip of the catheter device is used to make the initial penetrations in the stomach and intestines. After gaining access to the intestines 203 the catheter device 204 can deploy a distal flange of the stent 34 in the intestines 203 by withdrawing or retracting a sheath constraining the distal flange of the stent 34 as shown in FIG. 20A. After expansion of the distal flange of the stent 34 the stent 34, catheter device 203, and endoscope 200 are pulled proximally to pull the intestines 203 close to the stomach 201 at which point the grasper 202 can be released and withdrawn as shown in FIG. 20B. The proximal flange of the stent 34 can be deployed in the stomach 201 by continuing to retract the sheath constraining the stent 34. After deploying the stent 34 a pathway is formed through the interior of the stent between the stomach 200 and intestines 203 as shown in FIG. 20C. The stent flanges are designed such that food and partially digested food can flow through the internal volume of the stent. Optionally the stent can be balloon dilated after deployment to more quickly form the fully expanded configuration. After deployment of the stent the endoscope is removed. The stomach and intestine junction can heal to form an anastomosis. After formation of the anastomosis the stent can be endoscopically removed using a snare or other known technique.

Figures 21C, 21D:
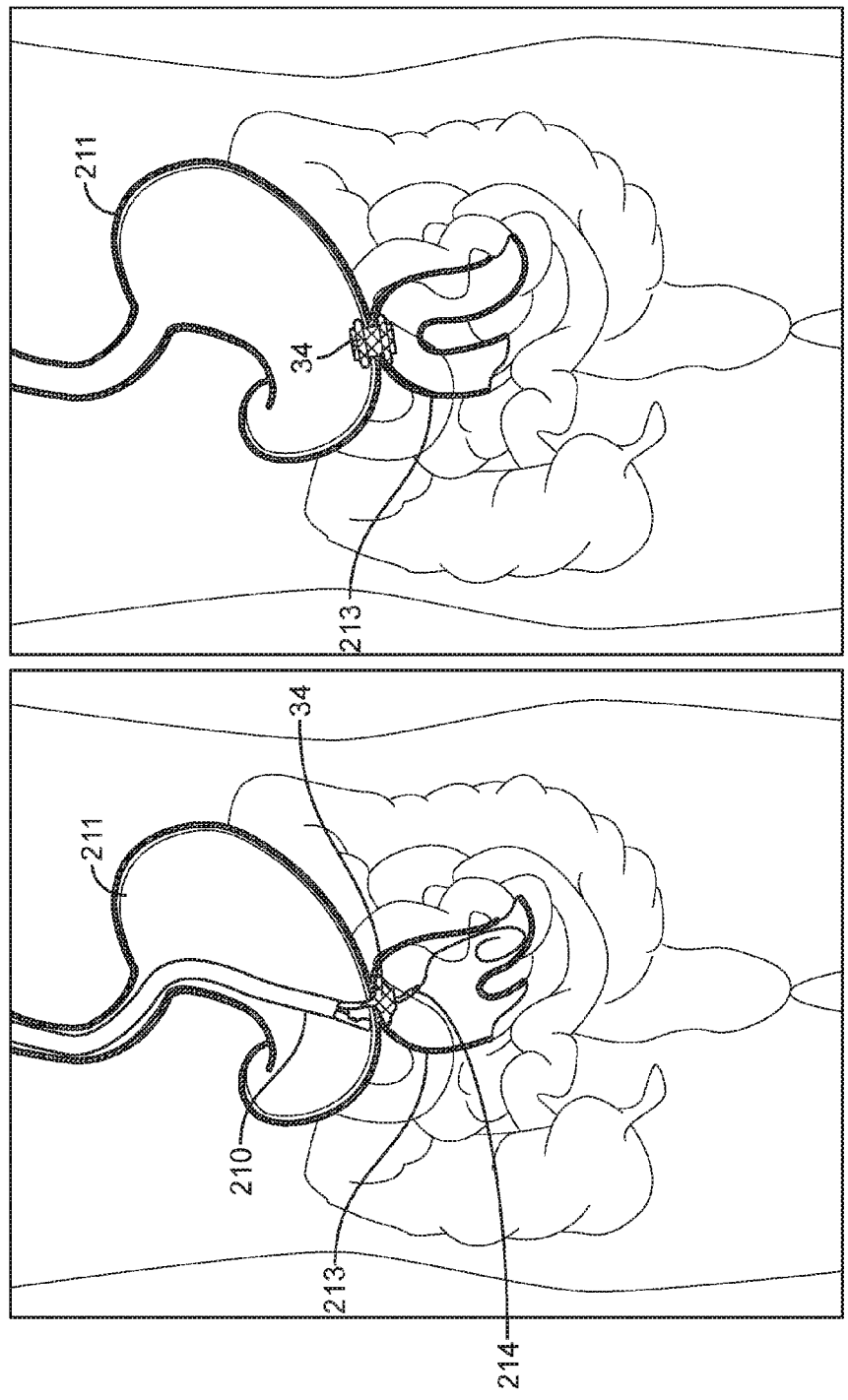

Current ultrasound endoscopes have one open lumen to pass a tool through. These ultrasound endoscopes do not have additional lumens to utilize additional tools. These endoscopes with ultrasound ability have ultrasound guidance can also be used to locate a target region in the intestines. FIGS. 21A-21C illustrate a method for deploying a stent between a stomach and a portion of the intestines using ultrasound guidance in accordance with some embodiments. The procedure illustrated in FIGS. 21A-21C can be referred to as a EUS (endoscopic ultrasound) procedure. The EUS procedure offers reduced risks of contamination of the peritoneal cavity in comparison to the NOTES procedures because a large gastric incision is not needed and the scope does not exit the stomach, and the target region in the intestines can be located ultrasonically, with less hunting around in comparison to using the endoscope to search within the peritoneal cavity to find the target region in the intestines.

An endoscope with ultrasound capabilities 210 enters the mouth and advances down the esophagus and into the stomach 211. There are many methods of creating an ultrasound target, for example an infusion catheter can be advanced through a port on the endoscope through the pyloric valve past the duodenum and advanced into a target location in the intestines 213. Once the infusion catheter is advanced to the target location in the intestines 213 a bolus of saline is injected. After injecting the saline the infusion catheter is removed. A needle 212 can then be advanced in the endoscope lumen. Ultrasound can be used to identify the section of the intestines 213 filled with saline as shown in FIG. 21A. Ultrasonic guidance is used to advance the needle 212 to initially puncture the stomach wall and the wall of the intestines to gain access to the intestines 213 followed by advancing a guidewire into the intestines. A catheter device 214 carrying a stent 34 can follow the guidewire to gain access to the target location in the intestines 213 as shown in FIG. 21B. In this embodiment needle access is preferred; however, in some embodiments the catheter can be used to make the initial penetrations in the stomach wall and intestines using the energized distal tip directly without a needle and guidewire. After gaining access to the intestines 213 the catheter device 214 can deploy a distal flange of the stent 34 in the intestines 213 by withdrawing or retracting a sheath constraining the distal flange of the stent 34 as illustrated in FIG. 21B. The catheter device 214 can be retracted proximally to pull the intestines 213 to be in apposition with the stomach 211 as shown in FIG. 21C. The proximal flange of the stent 34 can then be deployed in the stomach 211 by continuing to retract the sheath constraining the stent 34, as shown in FIG. 21D. After deploying the stent 34 a pathway is formed through the interior of the stent 34 between the stomach 211 and intestines 213. The stent flanges are designed such that food and partially digested food can flow through the internal volume of the stent. Optionally the stent can be balloon dilated after deployment to more quickly form the fully expanded configuration. After deployment of the stent the endoscope is removed. The stomach and intestine junction can heal to form an anastomosis. After formation of the anastomosis the stent can be endoscopically removed using a snare or other known technique.

Laparoscopic tools can also be used to assist a catheter device with locating and accessing portions of the body, such as the intestines and stomach. The intestines are in the peritoneal cavity in a disordered fashion. The ability to use a laparoscopic graspers and camera can improve locating and visualizing the target anatomy in the peritoneal cavity along with positioning the target anatomy in a desired orientation and position for the surgical procedure.

FIGS. 22A-22D illustrate a method for deploying a stent 34 between a stomach 221 and a portion of the intestines 223 using an endoscopic catheter 220 and laparoscopic tools 225, 226 in accordance with some embodiments. A plurality of laparoscopic ports can be used to assist the catheter device 224 in locating the target location of the intestines 223 and penetrating the intestines 223. A laparoscopic environment is created in the peritoneum. In one example, two tools and one camera can be used with a three laparoscopic port arrangement. A catheter device 224 (with or without an endoscope 220) enters the mouth and advances down the esophagus to the stomach. The catheter device 224 can include a fiber optic light that can shine through the stomach wall for visualization in the peritoneal cavity by the camera as described in FIG. 14. The light can facilitate identification of the location of the tip of the catheter prior to penetrating the wall of the stomach. The catheter tip can also be visualized by poking the stomach wall 221 with the catheter and using the laparoscopic tools to view where the catheter contacts the stomach wall 221. A tip of the laparoscopic tool 225 can contact the location of the stomach 221 wall being contacted by the catheter 224 to form an incision that allows the catheter to advance through the stomach wall as shown in FIG. 22A. In another embodiment the catheter 224 can include an energized tip to cut and penetrate the stomach wall 221. The laparoscopic tools 225, 226 can assist the catheter 224 to extend through the stomach wall 221. The laparoscopic camera can be used to identify the target section of the intestines 223. After locating the target section of the intestines the laparoscopic tools 225, 226 can hold the intestines 223 and assist the positioning of the tip of the catheter 224 adjacent to an exterior wall of the intestines 223 as shown FIG. 22A. The energized tip of the catheter device 224 can then be used to penetrate the wall of the intestines 223 or the laparoscopic tool 226 can be used to make an incision in the intestines 223 followed by advancing the catheter 224 into the intestines 223 as shown in FIG. 22B. After gaining access to the intestines 223 the catheter device 224 can deploy a distal flange of the stent 34 in the intestines 223 by withdrawing or retracting a sheath constraining the distal flange of the stent as illustrated in FIG. 22B. The catheter device 224 can be retracted proximally to pull the intestines 223 closer to the penetration of the stomach 221 as shown in FIG. 22C. After pulling the intestines 223 closer to the penetration in the stomach 221 the proximal flange of the stent 34 can be deployed in the stomach 221 by continuing to retract the sheath constraining the stent 34. After deploying the stent 34 a fluid conduit is formed through the interior of the stent 34 between the stomach 221 and intestines 223 as shown in FIG. 22D. The stent flanges are designed such that food and partially digested food can flow through the internal volume of the stent. Optionally the stent can be balloon dilated after deployment to more quickly form the fully expanded configuration. After deployment of the stent the endoscope is removed. The stomach and intestine junction can heal to form an anastomosis. After formation of the anastomosis the stent can be endoscopically removed using a snare or other known technique.

The above NOTES, EUS, laparoscopically assisted, laparoscopic catheter access methods are illustrated as forming an anastomosis between the stomach and intestines. The methods and steps apply equally to forming an anastomosis with a fundal pouch formed as part of a gastric bypass procedure. Using the stents disclosed herein for the anastomosis between the gastric pouch and the intestines forms a consistent size anastomosis and fluid conduit between the gastric pouch and intestines while greatly reducing the likelihood of leakage during the procedure. The procedure is quicker and less invasive than the conventional gastric bypass procedures and can be repeated with reliable and consistent anastomosis formation.

Figures 24A, 24B:
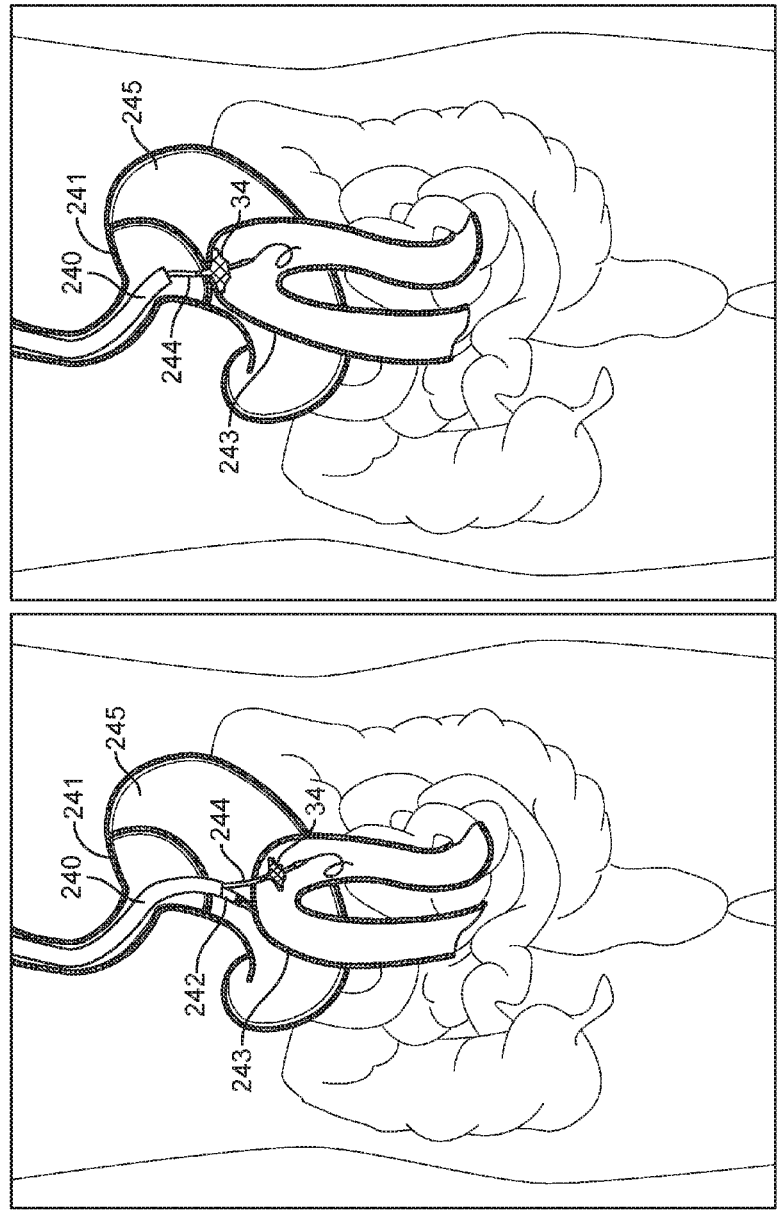
FIGS. 24A-24C illustrate a method for deploying a stent between a fundal pouch and a portion of the intestines in accordance with some embodiments.
Figure 24C:
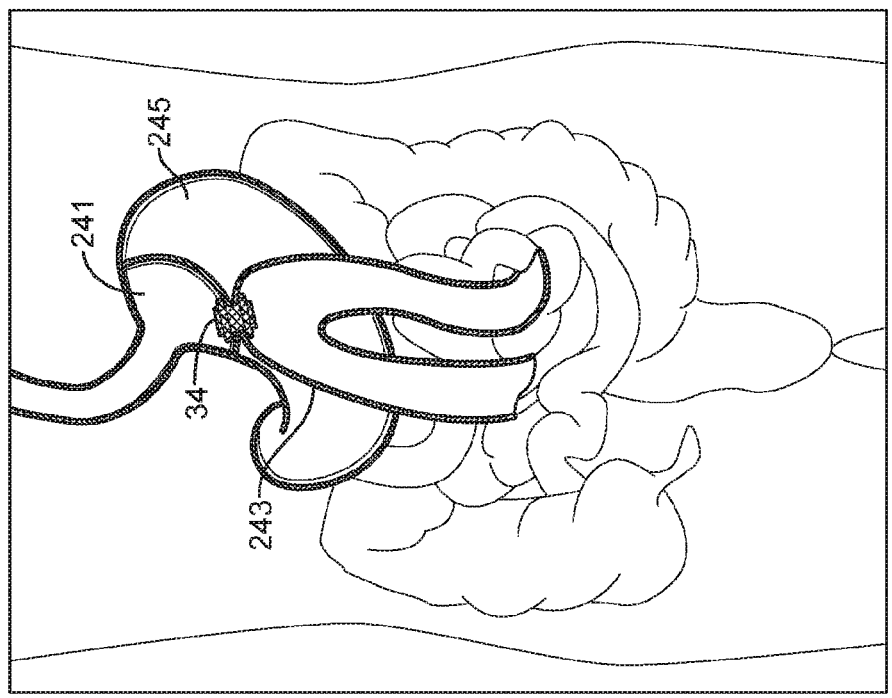

FIGS. 24A-24C illustrate a method for deploying a stent between a fundal pouch 241 and a portion of the intestines in accordance with some embodiments. The method illustrated in FIGS. 24A-24C is similar to the method illustrated in FIGS. 20A-20C but instead of an anastomosis between the stomach and intestines an anastomosis is formed between the fundal pouch 241 formed during a gastric bypass procedure and intestines 243. An endoscope enters the mouth and is advanced down the esophagus into the fundal pouch. The endoscope can include a plurality of ports. For example, one port can contain a catheter device carrying the stent and a second port can contain a grasper device and/or tools to create an incision. After making an incision in a fundal pouch an endoscope 240 is advanced through the penetration in the fundal pouch 241. The fundal pouch 241 is formed by stapling together the walls of the stomach to form a pouch 241 having a smaller volume than the full volume of the stomach thereby creating a bypassed portion of the stomach 245. FIG. 24A illustrates a grasper device 242 holding the intestines 243 adjacent to the target location of the intestines 243 to facilitate catheter 244 access to the intestines 243. The catheter 243 can follow a guidewire deployed after the initial access penetration formed by a needle (as illustrated) or an energized tip of the catheter 244 can be used for the initial penetration of the intestines 243. A distal end of the stent 34 is deployed within the intestines 243 as shown in FIG. 24A followed by pulling proximal traction on the catheter device 244 and distal flange of the stent to pull the intestines 243 closer to the fundal pouch 241 as shown in FIG. 24B. The sheath of the catheter 244 is further retracted to deploy the proximal end of the stent 34. After deployment of the proximal end of the stent 34 the endoscope 240 and catheter 244 are withdrawn from the fundal pouch 241 to leave the expanded stent 34 in place forming a pathway between the fundal pouch 241 and the intestines 243 as shown in FIG. 24C.

Figures 25A, 25B:
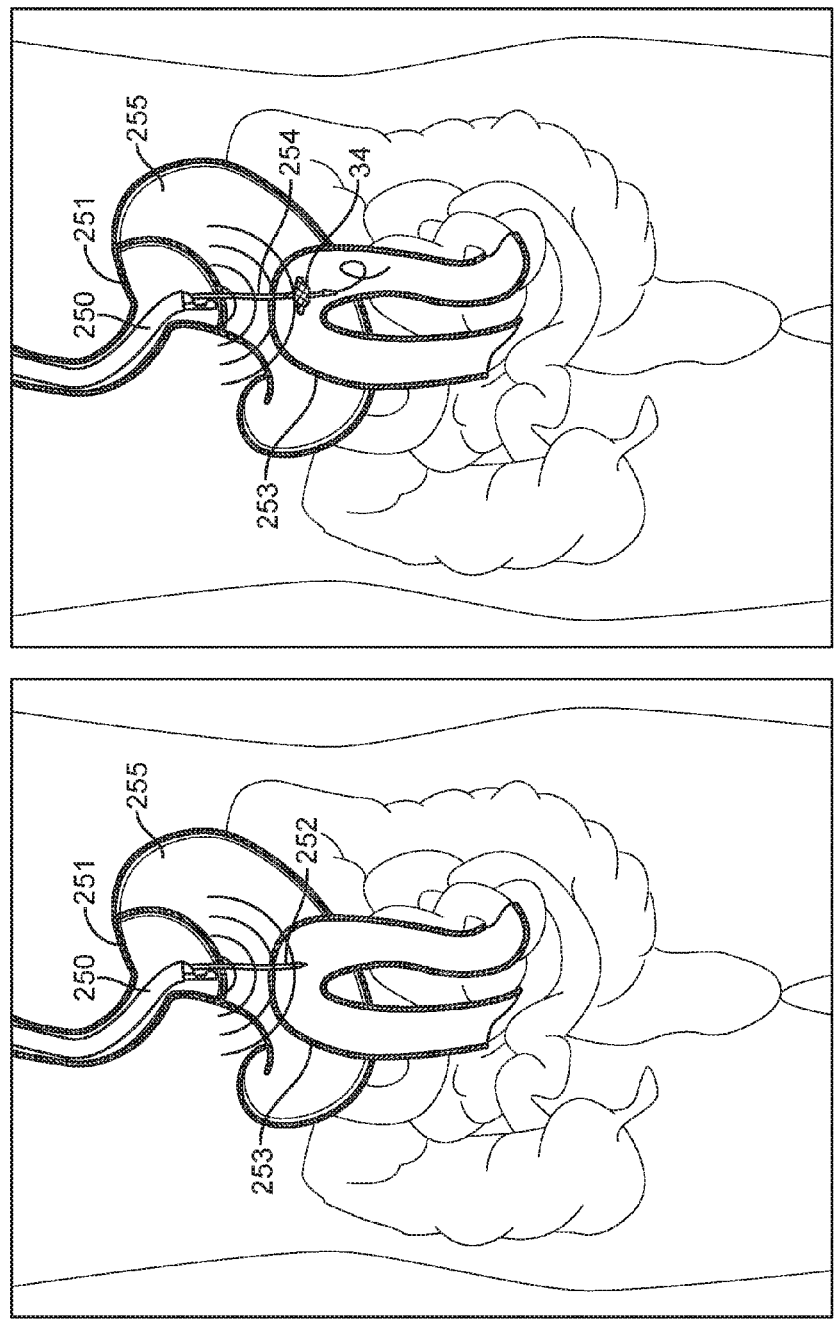
FIGS. 25A-25D illustrate a method for deploying a stent between a fundal pouch and a portion of the intestines using ultrasound guidance in accordance with some embodiments.
Figure 25D:
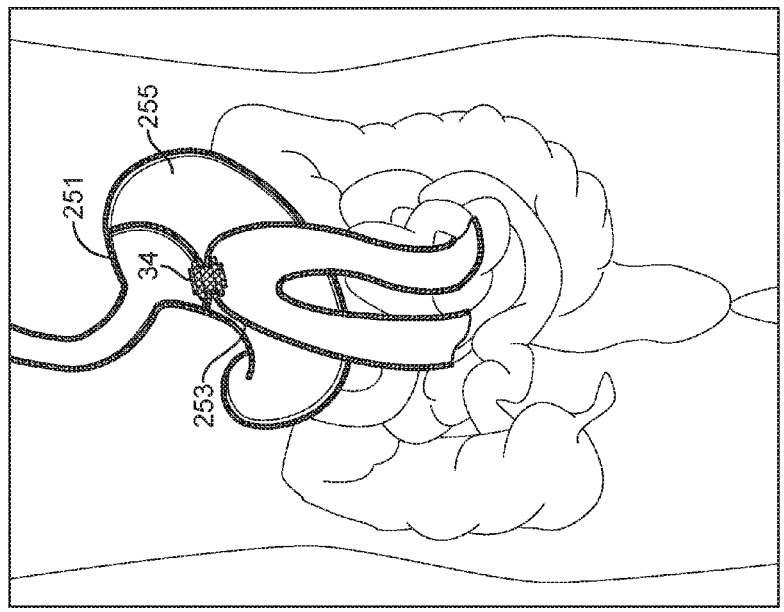
Figure 25C:
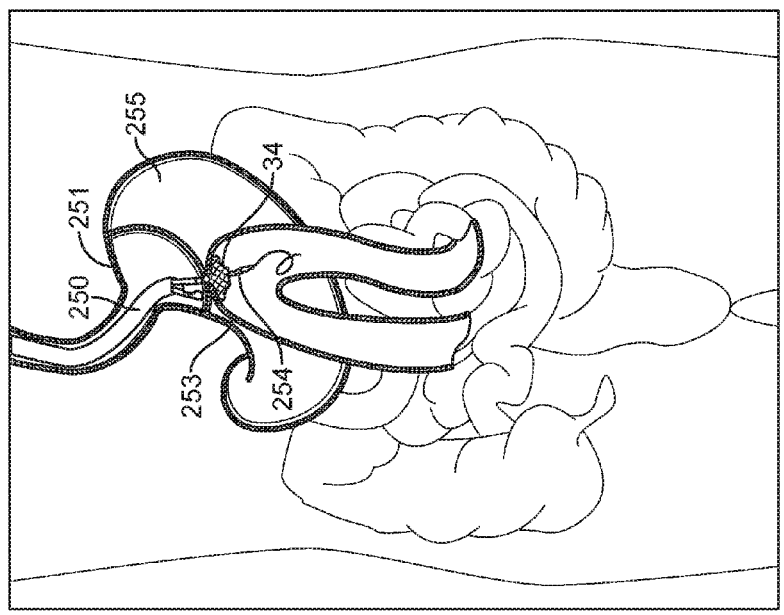

FIGS. 25A-25C illustrate a method for deploying a stent between a fundal pouch and a portion of the intestines using ultrasound guidance in accordance with some embodiments. The method illustrated in FIGS. 25A-25C is similar to the method illustrated in FIGS. 21A-21C but instead of an anastomosis between the stomach and intestines an anastomosis is formed between the fundal pouch and intestines. One difference between the methods illustrated in FIGS. 21A-21C is that the ultrasound marker, e.g. saline in the example described in FIGS. 21A-21C, is placed prior to forming the fundal pouch because the fundal pouch is stapled closed initially and is not in communication with the intestines. After formation of the fundal pouch 251 an ultrasound endoscope 250 carrying a catheter device 254 with a stent 34 is advanced through the mouth and esophagus to the fundal pouch 251. The bypassed portion of the stomach is illustrated as 255. Ultrasonic guidance is used to locate the marker in the intestines 253 and to advance a needle 252 to form an initial penetration in the wall of the fundal pouch 251 and the wall of the intestines 253 as shown in FIG. 25A. A guidewire can be deployed through the needle followed by withdrawing the needle. The catheter 254 can then follow the guidewire to access the intestines 253. A distal flange of the stent 34 is deployed by withdrawing the sheath of the catheter device 254 as shown in FIG. 25B. Proximal traction can be pulled on the distal flange of the stent 34 to pull the intestines 253 closer to the fundal pouch 251 as shown in FIG. 25C. The sheath of the catheter is further retracted to deploy the proximal end of the stent 34. After deployment of the proximal end of the stent 34 the endoscope 250 and catheter 254 are withdrawn from the fundal pouch 251 to leave the expanded stent 34 in place forming a pathway between the fundal pouch 251 and the intestines 253 as shown in FIG. 25D.

Figure 26A:
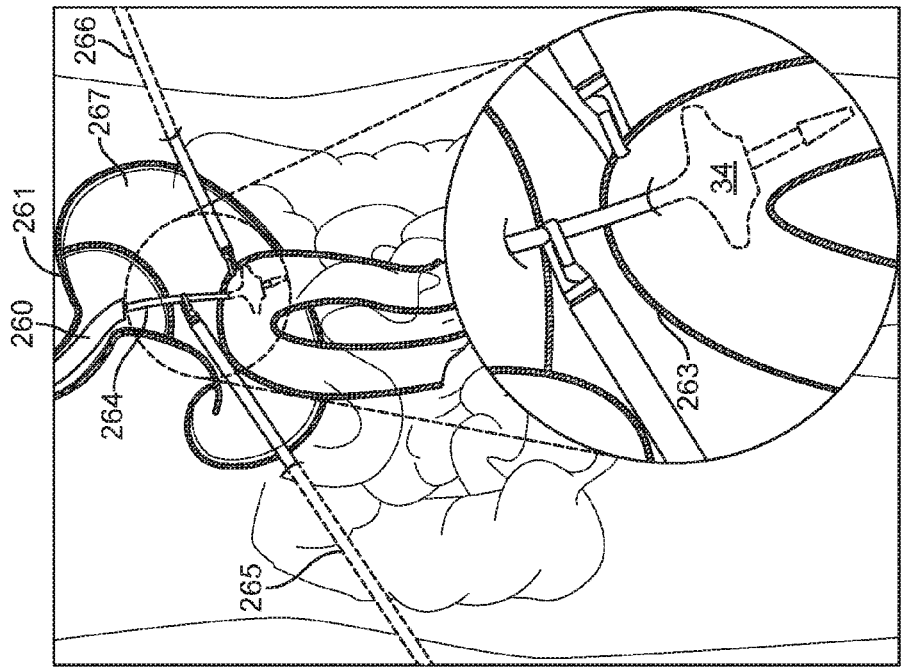
FIGS. 26A-26D illustrate a method for deploying a stent between a fundal pouch and a portion of the intestines using an endoscopic catheter and laparoscopic tools in accordance with some embodiments.
Figure 26B:
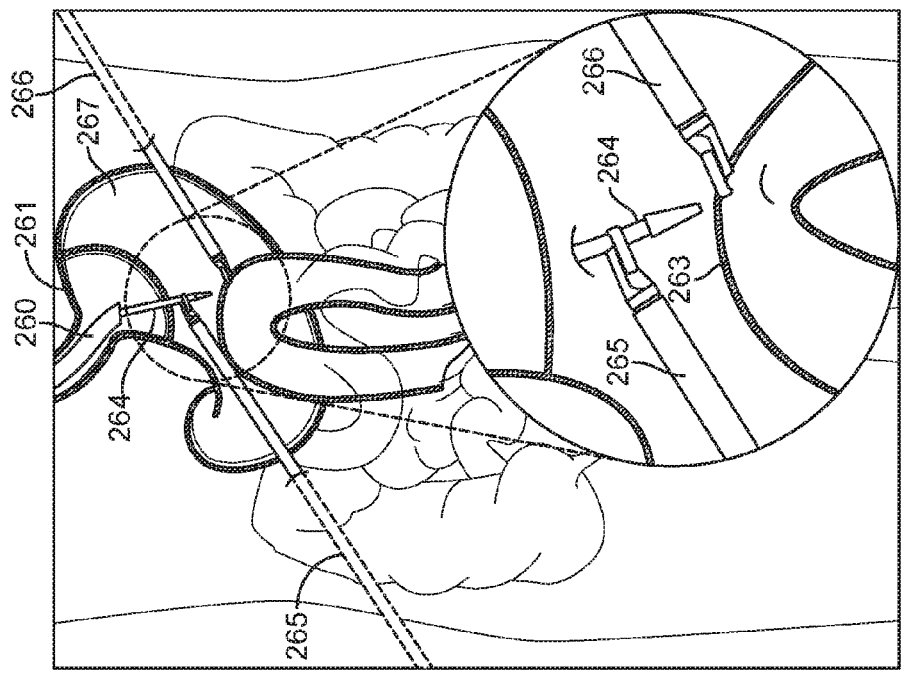
Figure 26D:
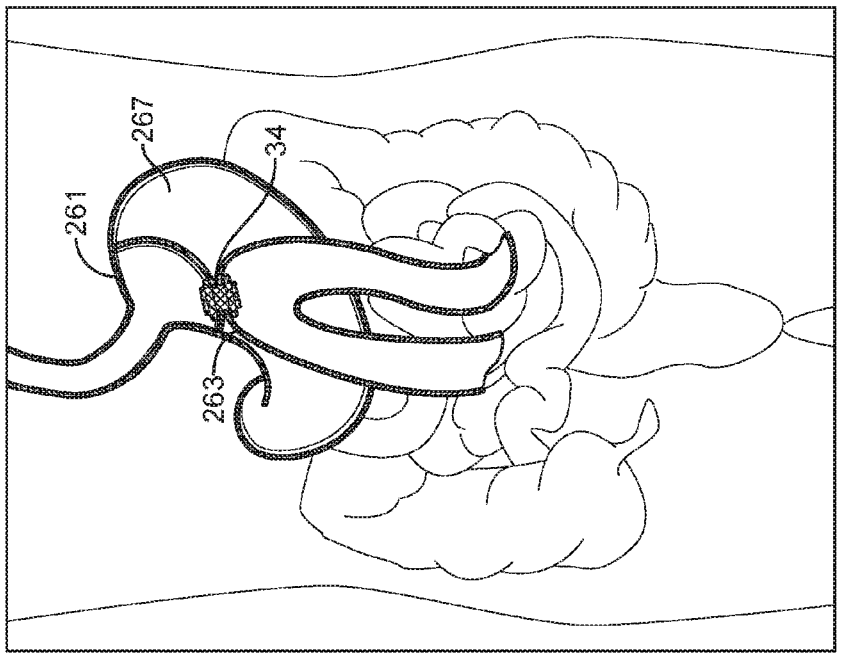
Figure 26C:
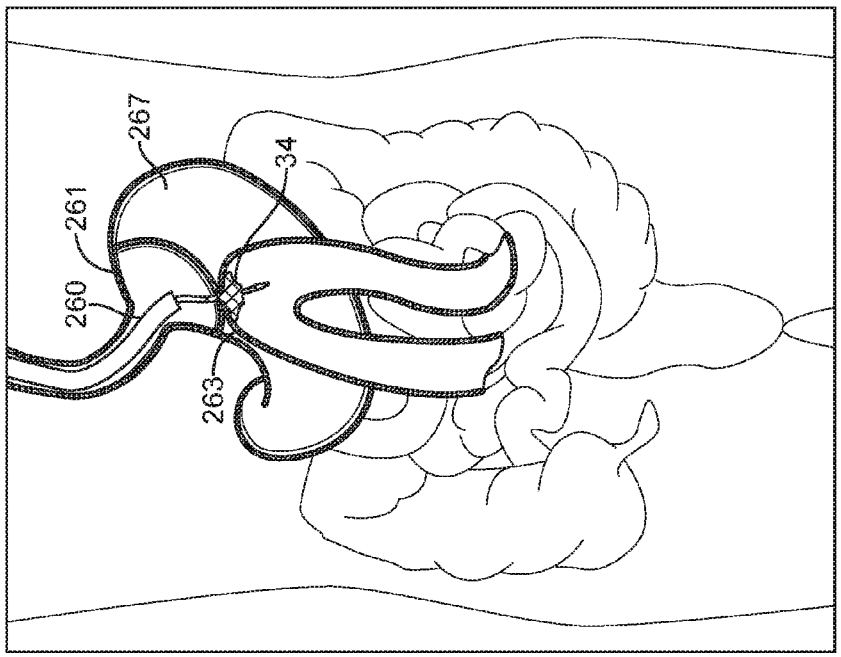

FIGS. 26A-26D illustrate a method for deploying a stent 34 between a fundal pouch 261 and a portion of the intestines using an endoscopic catheter 260 and laparoscopic tools 265, 266 in accordance with some embodiments. The method illustrated in FIGS. 26A-26D is similar to the method illustrated in FIGS. 22A-22D but instead of an anastomosis between the stomach and intestines an anastomosis is formed between the fundal pouch 261 and intestines 263. A catheter 264 is advanced to a desired location in the fundal pouch 261 followed by penetrating a wall of the fundal pouch 261 with the assistance of a laparoscopic tool. The bypassed portion of the stomach is illustrated as 267. Laparoscopic graspers 265, 266 are used to position the tip of the catheter device 264 relative to the target location in the intestines 263 as shown in FIG. 26A. The catheter 264 is advanced to penetrate a wall of the intestines 263 using an energized tip on the catheter device 264 or the penetration can be made using the laparoscopic tools 255 or 256 followed by withdrawing a sheath to deploy a distal flange of a stent 34 within the intestines 263 as shown in FIG. 26B. Proximal traction is pulled on the distal flange of the stent 34 and catheter 254 to pull the intestines 263 closer to the fundal pouch 261 as shown in FIG. 26C. The sheath can be further withdrawn to deploy a proximal flange of the stent 34 within the fundal pouch 261 thereby forming a pathway between the fundal pouch 261 and the intestines 263 as shown in FIG. 26D. After deploying the stent 34 the catheter is withdrawn from the fundal pouch 261.

The stents disclosed herein can also be used with conventional gastric bypass procedures. For example a stent can be placed in either of the anastomoses formed during the gastric bypass procedure, such as the stomach to jejunum anastomosis and duodenum to ileum anastomosis. The stents can be delivered endoscopically or laparoscopically (e.g. laparoscopic access through the peritoneal cavity to the intestines using the catheter device carrying the stent). The stents can improve healing of the anastomoses formed during the gastric bypass procedure while reducing the risk of leakage. The stents also promote formation of a healthy anastomosis. Furthermore, the stents can be quickly and easily deployed across the anastomoses formed between the stomach to jejunum and the duodenum to ileum.

Figure 2A:
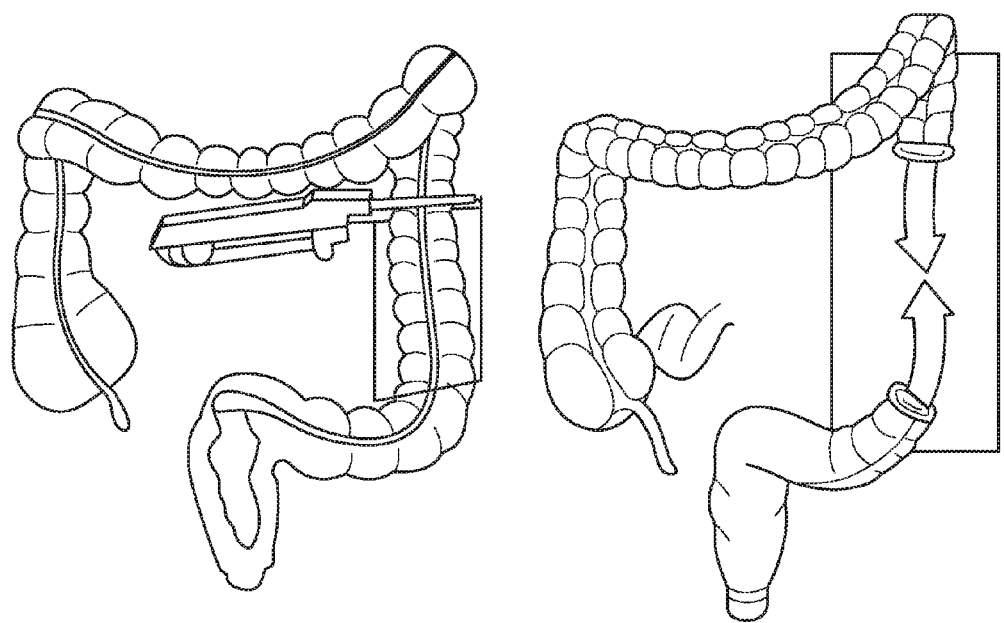
FIGS. 2A-2C illustrate schematic examples of colon resection surgery.
Figure 2B:
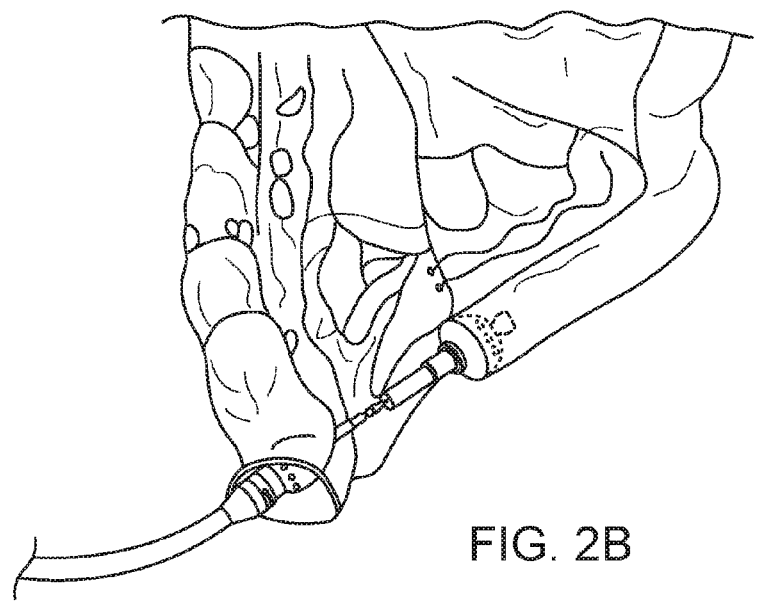
Figure 2C:
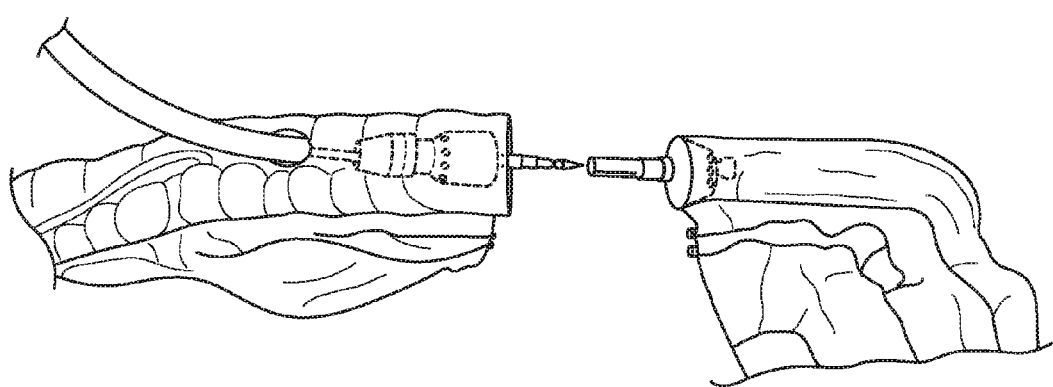
Figure 23A:
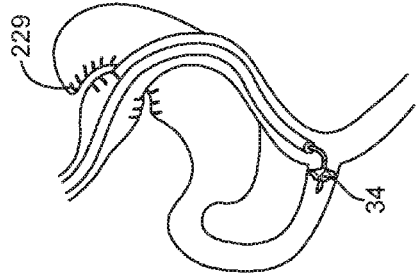
FIGS. 23A-23G illustrate a method for deploying an anastomotic stent between a fundal pouch and the jejunum and between a duodenum and ileum after a gastric bypass procedure in accordance with some embodiments.
Figure 23B:
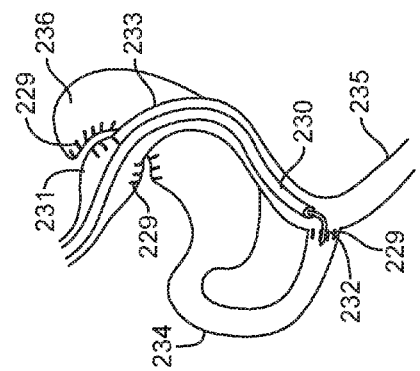
Figure 23C:
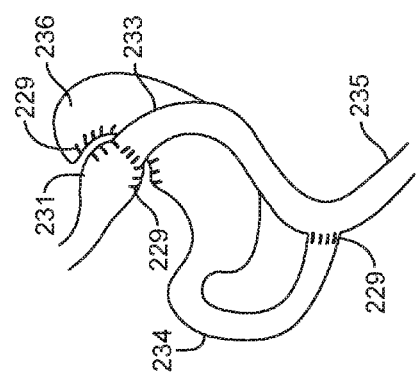
Figure 23G:
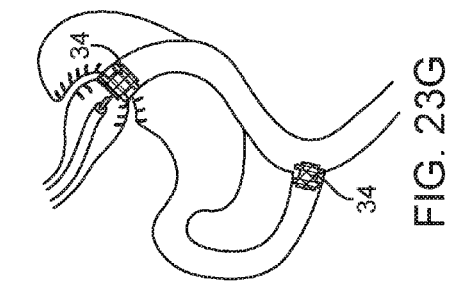
Figure 23F:
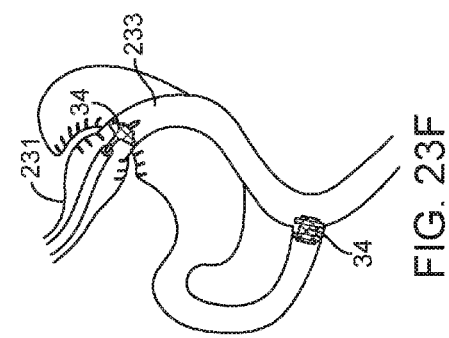
Figure 23E:
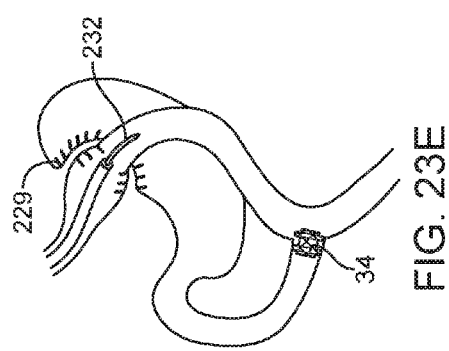
Figure 23D:
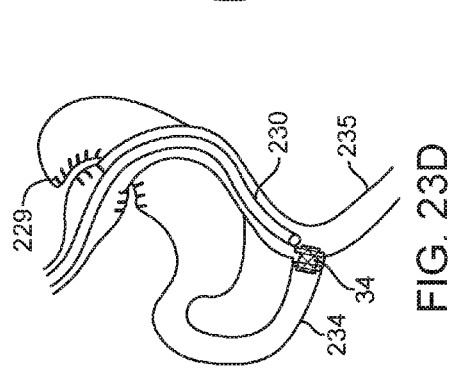

FIGS. 23A-23G illustrate a method for deploying an anastomotic stent between a fundal pouch and a section of the intestines, such as the jejunum and between two sections of the intestines, such as a duodenum and ileum after a gastric bypass procedure in accordance with some embodiments. Although described with reference to forming an anastomosis between the fundal pouch and jejunum and an anastomosis between the duodenum and ileum, the anastomosis can be formed between the fundal pouch and any portion of the intestines and between any two portions of the intestines. A conventional gastric bypass procedure is first performed to create the anastomoses using staples and sutures between the gastric pouch and a portion of the intestines, such as the jejunum and between two sections of the intestines, such as the duodenum and ileum. The gastric bypass procedure leaves behind suture or staple lines 229 having a known potential and risk of leakage as shown in FIG. 23A. The anastomotic stents described herein can be deployed at the anastomosis between the fundal pouch and jejunum and at the anastomosis between the duodenum and ileum to reduce the chance of leakage at the anastomoses. The staple lines 229 are omitted in FIGS. 23B-23G across the connections between the fundal pouch and jejunum and duodenum and ileum to facilitate the illustration of the deployment of the stents at those sites. The stent is not deployed through or across the staple or suture lines but is instead deployed adjacent to the staple or suture lines. FIG. 23B illustrates advancing an endoscope 230 through the fundal pouch 231 and jejunum 233 to the anastomoses between the duodenum 234 and ileum 235. The bypassed stomach 236 is stapled adjacent to the fundal pouch 231. The stent 34 is deployed from the catheter 232 as shown in FIGS. 23C-23DC between the duodenum 234 and ileum 235. The endoscope 230 is retracted to the anastomosis between the fundal pouch 231 and jejunum 233 as shown in FIG. 2ED. The first catheter is removed and a second catheter is put in place. The stent 34 is deployed between the fundal pouch 231 and jejunum 233 using the second catheter as shown in FIGS. 23F-23G.

The stent can also be deployed using two devices as shown in FIGS. 19B-19D. The stent illustrated in two halves (FIG. 19A) can be deployed using a separate device for each half. One end of the stent can be deployed as shown in FIGS. 19B-C. After both halves are deployed the magnetic ring or other connection mechanism can be used to connect the two halves and form the anastomosis as shown in FIG. 19D. The first portion of the device can be deployed from the esophagus and the other portion of the device can be inserted laparoscopically or through another natural orifice, such as the rectum.

Sealed off portions of the intestines are evident when for example performing a resection procedure. During such resection procedures standard surgical tools are used to form a linear double staple line followed by cutting between the staple lines. This forms two ends of the intestines at the incision point. This can be performed, for example, at two locations in the intestines allowing the surgeon to remove the segment between the two cut lines thereby leaving two sealed off portions of the intestines that need to be joined. Methods for forming an anastomosis between two sealed off portions of the intestines, (such as the colon and rectum), are disclosed herein. FIGS. 27A-27F and 30A-30F illustrate methods for forming an anastomosis between two sealed off portions of the intestines.

Figure 27A:
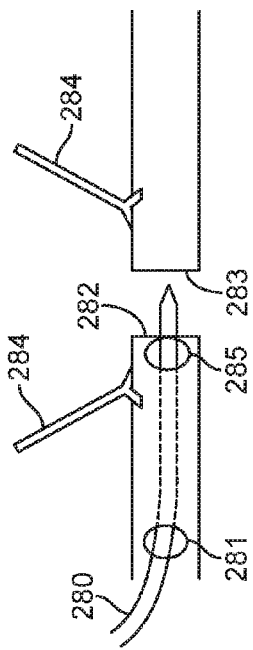
FIGS. 27A-27E illustrate a method for forming an anastomosis between two sealed off portions of the intestines in accordance with some embodiments.
Figure 27B:
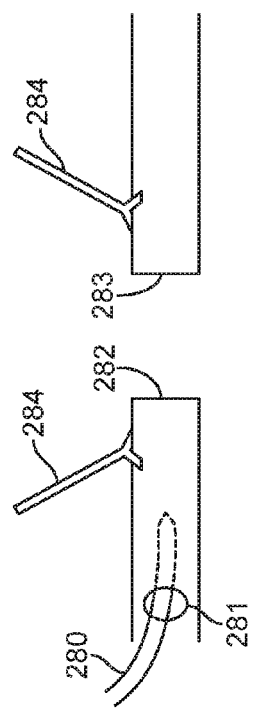
Figure 27C:
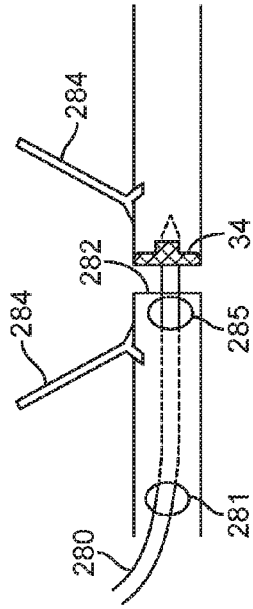
Figure 27D:
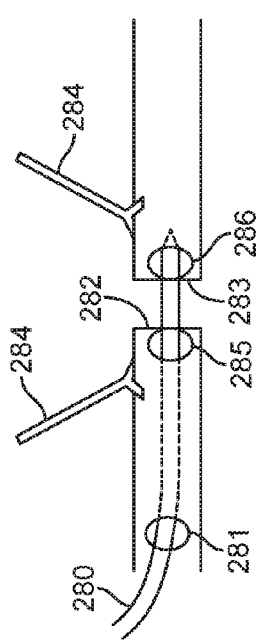
Figure 27E:
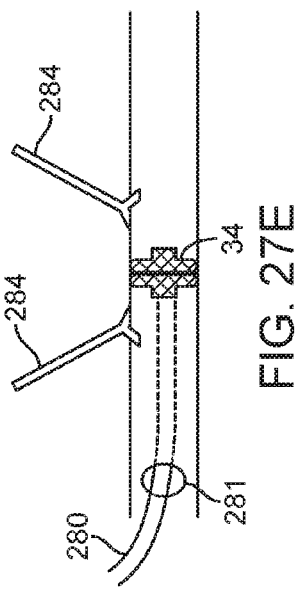

FIGS. 27A-27F illustrate a method for forming an anastomosis between two sealed off portions of the intestines using a catheter to access a portion of the intestines through the peritoneal cavity. Two sealed off ends of the colon 282, 283 are formed during a portion of a colon resection procedure as described above. A catheter 280 then enters the peritoneal cavity and enters the intestines at a target penetration 281 as shown in FIG. 27A. Laparoscopic tools 284, illustrated as graspers can be used to facilitate navigation of the catheter 280. The catheter 280 is advanced as shown in FIG. 28B to penetrate the colon at penetration 285, which is adjacent to the first sealed off end of the colon 282. The penetration is not made through the stapled or sutured end. The catheter can use an energized tip to make the penetration 285. The catheter is then advanced to penetrate the second portion of the colon at penetration 286 with the graspers 284 used to position the colon as shown in FIG. 28C. The distal flange of the stent 34 is deployed by withdrawing a sheath on the catheter. The stent 34 is deployed in the colon such that it engages the colon wall as shown in FIG. 28D. Proximal traction is pulled on the catheter 280 and stent 34 to pull the colon closer to penetration 285 followed by deploying the proximal end of the stent 34 within the first section of the colon as shown in FIG. 28E. The same procedure can be followed to utilize the standards surgical tools for forming the fundal pouch to create the anastomosis between the fundal pouch and intestines (e.g. not going through the staple lines).

Laparoscopic tools can also be used to access the peritoneal cavity and to deploy a stent to form an anastomosis between any portions of the gastro-intestinal tract. FIGS. 28A-28G, 29A-29G, and 30A-30F illustrate methods for using laparoscopic stent delivery devices to deploy stents between body lumens in the GI tract.

FIGS. 28A-28G illustrate a laparoscopic method for deploying a stent between a stomach and a portion of the intestines using the laparoscopic device 50 illustrated in FIG. 5A-5C. A laparoscopic environment is created in the peritoneal cavity and a laparoscopic device 50 enters the peritoneal cavity (FIG. 28A). The target body lumens are located, in this example the stomach 291 and intestines 292. A penetration 293 is made in the stomach 291 using endoscopic or laparoscopic tools. The orientation of the stent holder of the device 50 is adjusted to facilitate positioning an end of the stent 34 within the penetration 293 of the stomach 291 (FIG. 28B). Next, the stent 34 end enters the stomach 291 through the penetration 293 (FIG. 28C). The radial restraint, illustrated as shrink wrap tubing can be released using a rip cord type mechanism. Removing the shrink wrap allows the stent 34 to adopt an expanded configuration inside the stomach 291 as shown in FIG. 28D. A penetration 294 is made in the intestines 292 using endoscopic or laparoscopic tools. Next, the other end of the stent 34 can be deployed inside the intestines 292 using a similar methodology as shown in FIGS. 28D-28F. FIGS. 28D-28E illustrate placing the second end of the stent 34 through the penetration 294. The radial restraint is removed to allow the second flange of stent 34 to deploy within the intestines 292 (FIG. 28F). After the distal and proximal ends of the stent 34 have been deployed the device 50 releases the grip on the stent 34. After the stent 34 is released by the device 50, the device 50 can be removed from the peritoneal cavity along with cut radial restrain and cords or pull-wires used to cut the radial restraint.

FIGS. 29A-29G illustrate a laparoscopic method for deploying a stent between a fundal pouch and a portion of the intestines using the laparoscopic device 50 illustrated in FIG. 5A-5C. FIGS. 29A-29G are similar to FIGS. 28A-28G but with forming an anastomosis between the fundal pouch and intestines instead of the stomach and intestines. A laparoscopic environment is created in the peritoneal cavity and a laparoscopic device 50 enters the peritoneal cavity (FIG. 29A). The target body lumens are located; in this example the fundal pouch 301 and intestines 302. A penetration 303 is made in the fundal pouch 301 using endoscopic or laparoscopic tools. The orientation of the stent holder of the device 50 is adjusted to facilitate positioning an end of the stent 34 within the penetration 303 of the fundal pouch 301 (FIG. 29B). Next, the stent 34 ends enters the stomach 301 through the penetration 303 (FIG. 29C). The radial restraint, illustrated as shrink wrap tubing can be released using a rip cord type mechanism. Removing the shrink wrap allows the stent 34 to adopt an expanded configuration inside the fundal pouch 301 as shown in FIG. 29D. A penetration 304 is made in the intestines 302 using endoscopic or laparoscopic tools. Next, the other end of the stent 34 can be deployed inside the intestines 302 using a similar methodology as shown in FIGS. 29D-29F. FIGS. 29D-29E illustrate placing the second end of the stent 34 through the penetration 304. The radial restraint is removed to allow the second flange of stent 34 to deploy within the intestines 302 (FIG. 29F). After the distal and proximal ends of the stent 34 have been deployed the device 50 releases the grip on the stent 34. After the stent 34 is released by the device 50, the device 50 can be removed from the peritoneal cavity along with cut radial restrain and cords or pull-wires used to cut the radial restraint.

FIGS. 30A-30F illustrate a laparoscopic method for deploying a stent between two sealed off sections of the intestines, that can be formed as described above, using the laparoscopic device 50 illustrated in FIG. 5A-5C. A laparoscopic environment is created in the peritoneal cavity and a laparoscopic device 50 enters the peritoneal cavity (FIG. 30A). The target body lumens are located, in this example the cut and sealed ends of the colon, 310 and 311. A first penetration 312 is made adjacent to the first sealed end 310 of the colon and a second penetration 313 is made adjacent to the second sealed end 311 of the colon using endoscopic or laparoscopic tools. The penetrations 312, 313 are made through the walls of the colon and are not made through the stapled and sealed ends 310, 311. The orientation of the stent holder of the device 50 is adjusted to facilitate positioning an end of the stent 34 within the penetrations 312 and 313 of the colon (FIG. 30B). Next, the stent 34 end enters the first end of the colon through the penetration 312 (FIG. 30C). The radial restraint, illustrated as shrink wrap tubing can be released using a rip cord type mechanism. Removing the shrink wrap allows the stent 34 to adopt an expanded configuration inside the first end of the colon as shown in FIG. 30D. Next, the other end of the stent 34 can be deployed inside the second end of the colon using a similar methodology as shown in FIGS. 30D-30F. FIGS. 30D-30E illustrate placing the second end of the stent 34 through the penetration 313. The radial restraint is removed to allow the second flange of stent 34 to deploy within the second end of the colon (FIG. 28E). After the distal and proximal ends of the stent 34 have been deployed the device 50 releases the grip on the stent 34. After the stent 34 is released by the device 50, the device 50 can be removed from the peritoneal cavity along with cut radial restraint and cords or pull-wires used to cut the radial restraint leaving just the stent 34 forming the pathway between the first end of the colon and the second end of the colon (FIG. 30F)

Although FIGS. 28-30 are illustrated using the laparoscopic device 50, any of the laparoscopic stent delivery devices disclosed herein can be used in those methods.

Although discussed in detail with reference to gastric bypass surgery and colon resection surgeries, the methods and devices can be used herein for forming any surgical anastomosis. Embodiments can be used to attach a ureter to a new part of the bladder. Embodiments can also be used to form an anastomosis between the rectum and another body lumen. Embodiments can also be used to form an anastomosis between the esophagus and another body lumen. Embodiments can be applied to ERCP applications where there is a need to access target anatomical structures through multiple tissue planes from a guidewire access. Embodiments are useful for applications and procedures, such as transduodenal, transgastric, biliary, pancreatic pseudocysts, transhepatic, transcystic, transpancreatic, transenteric, transbiliary, transsesophageal, transbronchial, transgastric, jejunostomy, transcolonic, etc.

In some embodiments the methods and devices can be used for peritoneal access and TIPS (transjugular intrahepatic portosystemic shunt). In some embodiments the methods and devices can be used in applications and procedures, such as for vascular access, arterial to vascular, pericardial access, and venus insufficiently via transvalve access.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Although the foregoing invention has been described in some detail by way of illustration and example, for purposes of clarity of understanding, it will be obvious that various alternatives, modifications and equivalents may be used and the above description should not be taken as limiting in scope of the invention which is defined in part by the appended claims.

What is claimed is:

1. A device having a self-expanding body that comprises:
a cylindrical middle region having a lumen and defining a longitudinal axis and a center plane perpendicular to the longitudinal axis;
a proximal end region and a distal end region that flare away from the longitudinal axis into flange configurations on opposite ends and around a full circumference of the cylindrical middle region when expanded;
each flange configuration comprising at least first and second points of inflection that define first and second segments of the flange;
the first segment extending from the first inflection point toward the center plane, the second segment extending from the second inflection point away from the center plane; and
wherein an angle of the first inflection point defined by the first segment and the cylindrical middle region is at least as great as an opposing angle of the second inflection point defined by the first segment and the second segment.

2. The device of claim 1, wherein the first and second segments are curved along a portion of the length of each segment.

3. The device of claim 1, wherein the first and second inflection points have a curved surface.

4. The device of claim 3, wherein the curved surfaces of the first inflection points of each flange face away from the center plane and the curved surfaces of the second inflection points of each flange face toward the center plane.

5. The device of claim 1, wherein a line passing through at least a portion of each flange configuration along a plane perpendicular to the longitudinal axis will intersect the flange configuration at four discrete points.

6. The device of claim 1, wherein the first and second inflection points and first and second segments of each flange configuration above or below the longitudinal axis form an S-shape or Z-shape.

7. A drainage stent having a self-expanding stent body that comprises:
a cylindrical middle region having a lumen and defining a longitudinal axis;
proximal and distal end regions that extend radially from the longitudinal axis into flared flange configurations on opposite ends and around a full circumference of the cylindrical middle region when expanded, each flared flange configuration defining at least first and second segment lengths of the stent body, the first segment lengths of the proximal and distal end regions extending in a direction toward each other along the longitudinal axis, and the second segment lengths of the proximal and distal end regions extending in a direction different than their respective first segment lengths;
wherein the first segment lengths of each flange configuration extend from the cylindrical middle region and the second segment lengths of each flange configuration extend from respective first segment lengths;
wherein the intersection of the cylindrical middle region and the first segment lengths defines a first inflection point and the intersection of the first segment lengths and second segment lengths defines a second inflection point; and
wherein an angle of the first inflection point defined by the first segment length and the cylindrical middle region is 90 degrees or less, and an opposing angle of the second inflection point defined by the first segment length and the second segment length is 90 degrees or less.

8. The drainage stent of claim 7, wherein the second segment lengths are shorter than the first segment lengths.

9. The drainage stent of claim 7, wherein the first and second inflection points and first and second segment lengths of each flange above or below the longitudinal axis form an S-shape or Z-shape.

10. The drainage stent of claim 7, wherein an end of the first segment length of each flange that is furthest from the longitudinal axis terminates at a distance along the longitudinal axis that is closer to a center plane of the cylindrical middle region than the first inflection point.

11. A drainage device having a device body that comprises:
a cylindrical middle region having a lumen and defining a longitudinal axis and a center plane perpendicular to the longitudinal axis;
proximal and distal end regions that flare radially from the longitudinal axis into flanges on opposite ends and around a full circumference of the cylindrical middle region when expanded, each flange comprising at least first and second points of inflection that define first and second segments of the flange, the second points of inflection being further spaced radially from the longitudinal axis than the first points of inflection, and the second points of inflection closer than the first points of inflection to the center plane along the longitudinal axis; and wherein the flanges on the opposite ends of the cylindrical middle region touch planes that are parallel to the longitudinal axis, at least one plane each above and below the longitudinal axis, at at least two separate points along the parallel planes.

12. The device of claim 11, wherein the device body is self-expanding and comprises a woven nitinol filament braid of a shape memory material.

13. The device of claim 12, wherein the woven nitinol filament braid comprises multiple filaments or a single filament.

14. The device of claim 11, further comprising an elastomeric material covering at least the cylindrical middle region of the device body.

15. The device of claim 11, wherein the first and second inflection points have curved surfaces that face in different directions with respect to the center plane.

* * * * *